United States Patent
Hasebe et al.

[11] Patent Number: 5,770,187
[45] Date of Patent: Jun. 23, 1998

[54] POROUS PARTICULATE AND COSMETIC

[75] Inventors: Yoshihiro Hasebe; Michitaka Sawada, both of Wakayama; Makoto Furukawa, Sumida-ku; Takako Nakayama, Wakayama; Kenji Kodama, Sumida-ku; Yasushi Ito, Wakayama; Genichi Nakamura, Wakayama; Yasuhisa Fukumoto, Wakayama, all of Japan

[73] Assignee: Kao Corporation, Tokyo, Japan

[21] Appl. No.: 702,699

[22] PCT Filed: Mar. 17, 1995

[86] PCT No.: PCT/JP95/00489

§ 371 Date: Sep. 13, 1996

§ 102(e) Date: Sep. 13, 1996

[87] PCT Pub. No.: WO95/25752

PCT Pub. Date: Sep. 28, 1995

[30] Foreign Application Priority Data

Mar. 18, 1994 [JP] Japan ..................... 6-048792
Mar. 31, 1994 [JP] Japan ..................... 6-062401

[51] Int. Cl.[6] .................................. A61K 7/035
[52] U.S. Cl. ................... 424/69; 424/400; 424/401; 514/951
[58] Field of Search ................. 514/951; 424/400, 424/401, 69

[56] References Cited

FOREIGN PATENT DOCUMENTS

| | | |
|---|---|---|
| 62-190110 | 8/1987 | Japan . |
| 63-290808 | 11/1988 | Japan . |
| 4-235906 | 8/1992 | Japan . |

OTHER PUBLICATIONS

Kobunshi Ronbunshu, vol. 37, No. 3, pp. 185–190 (Mar., 1980).

*Primary Examiner*—Terressa Mosley
*Attorney, Agent, or Firm*—Oblon, Spivak, McClelland, Maier & Neustadt, P.C.

[57] ABSTRACT

An amphoteric porous particulate containing a basic polysaccharide and a polymer of an organic acid containing a reactive vinyl group or a salt thereof and having an average particle size of 50 $\mu$m or less, is capable of adsorbing a large amount of an acid or a base that is stronger than the acid or basic groups thereof and is useful in a deodorant or a cosmetic. The amphoteric porous particulate is made by emulsifying or suspending an aqueous solution containing a basic polysaccharide and an organic acid having a reactive vinyl group in a hydrophobic solvent, followed by polymerization. A deodorant may be made of a chitosan particulate having an average particle size of 0.01 to 50 $\mu$m. A polysiloxane having long-chain alkyl groups and a melting point of 20° C. or above is useful as an oil component of a deodorant.

26 Claims, 1 Drawing Sheet

AMOUNT OF 4-PHENYLBUTYRIC ACID ADDED PER g OF CHITOSAN PARTICULATE

POROUS PARTICULATE AND COSMETIC

FIELD OF INDUSTRIAL APPLICATION

The present invention relates to a porous particulate which is useful in skin cosmetics (antiperspirants, deodorants, packs and humectants), hair care products, drugs, fiber treatments, paper coatings, cement additives, covering materials, bactericides/bacteriostats and agricultural chemicals.

PRIOR ART

The anionic/cationic amphoteric particulate derived through emulsification, suspension or the like is generally obtained by copolymerization of a monomer having an amino group and a monomer having an acidic group, or first forming an anionic or a cationic particulate and subsequently conducting a modification reaction to thereby convert a part of the reactive groups to cationic or anionic groups, or effecting compounding to thereby render cationic and anionic substances copresent.

These techniques, however, do not give a porous particulate, and the amount of basic and acid groups per particle which react with strong acids and bases is extremely small.

Further, processes for producing particulates with the use of natural raw materials include those in which chitosan having a primary amino group as a base is dissolved in an acid and the resultant solution is dropped into an alkaline coagulation fluid and those in which chitosan solutions or dispersions are mechanically treated. However, all the obtained particulates are cationic, and only particles with a diametrical size of tens to hundreds of micrometers or more can be obtained thereby. Still further, a granular complex of chitosan and an organic acid polymer is synthesized by a technique in which an organic acid having a reactive vinyl group is (co)polymerized in the presence of chitosan in an aqueous solution among various known techniques for producing amphoteric particles from basic polysaccharides as bases (see Kobunshi Ronbunshu (Reports of Polymer Science), Vol. 37, No. 3, 185 (1980)). However, the chitosan particulate produced by the above technique has a broad particle size distribution and only nonspherical particles containing particles with a size of 50 μm or greater can be obtained. Furthermore the porosity thereof is low.

Thus, no amphoteric porous particulate capable of adsorbing a large amount of an acid or base stronger than the acid or basic groups thereof and having an average particle size of 50 μm or less has been obtained.

If the above porous particulate capable of adsorbing a large amount of a strong acid or base is obtained, it would be useful in deodorants and the like with the use of the adsorptiyity thereof.

Body smells such as axillary, foot and sweat smells are unpleasant and serious distress to those having such smells. The components of body smells are metabolites produced by the action of resident bacterial flora of the skin upon smell-causing sweat, egesta, putrefied matter and the like. Thus, although the secreted sweat per se does not cause strong smell, it generates lower carboxylic acids and volatile matter, which cause offensive smells, by the action of the resident bacterial flora of the skin. It is known that the foul-smelling matter may be various and, for example, composed of a lower carboxylic acid such as acetic, butyric, propionic or isovaleric acid or a steroid.

Examples of the techniques for inhibiting the above body smells include a method (1) in which use is made of a metallic oxide such as zinc oxide, magnesium oxide, titanium oxide or alumina, a method (2) in which the physical adsorption of a porous substance such as active carbon is utilized, a method (3) in which use is made of an antibacterial drug capable of inhibiting the proliferation of the resident bacterial flora of the skin (for example, triclosan, isopropylmethylphenol, benzalkonium chloride, chlorhexidine, chlorhexidine gluconate or halocarban), a method (4) in which use is made of a strongly astringent drug (for example, zinc p-phenolsulfonate, citric acid, aluminum salt or zirconium salt), and masking by perfumes (5).

However, the physical deodorization using active carbon or the like has drawbacks not only in that the capacity of adsorbing lower fatty acids is not satisfactory but also in the comfort in the use thereof and the persistence of the effect thereof. Although the sensory deodorization such as masking by the use of a perfume changes the quality of smelling substances by means of the perfume, its method effect is limited because smelling substances are still left. On the other hand, the method using a metallic oxide such as zinc oxide, magnesium oxide, titanium oxide or alumina is not fully satisfactory because, although various measures for increasing the surface area of the metallic oxide have been taken to cope with the reaction of the metallic oxide with acids only on the surface of the metallic oxide, gelation is caused by the reaction of the metallic oxide with acids as foul-smelling substances despite the increase of the surface area of the metallic oxide, so that the capacity is poor for capturing acids generated with the passage of time.

With respect to the water-soluble acid salts of chitosan, Japanese Patent Laid-Open No. 290808/1988 discloses a deodorant and bactericidal cosmetic, whose deodorant effect is, however, little if any. With respect to the chitosan particulate, Japanese Patent Laid-Open Nos. 190110/1987 and 235906/1992 describe that the addition thereof to cosmetics such as foundations and eye shadows improves the comfort in the use of the cosmetics and the make-up, stability and moldability of the cosmetics. In the literature, however, there is no description regarding the use of the chitosan particulate in deodorants.

When applied to the skin by, for example, coating, the deodorant forms some film on the skin, thereby playing a role to help to prevent the scattering of active ingredients by means of the film formed on the skin.

However, most of the conventional deodorants are each composed mainly of water, an alcohol, an oil or the like, so that they are likely to flow by means of sweat or sebum, being sticky to the touch, and are likely to diffuse. Therefore, most of them do not have satisfactory film-forming capacity, thereby being poor in the effect of persistently holding the active ingredients thereof on the skin.

Paraffin wax, vaseline and other compounds that are solid or semisolid at room temperature are being employed as film formers. Although their film-forming effects are so high as to ensure a prolonged holding of active ingredients, they prevent the cutaneous respiration and the evapotranspiration of steam. Thus, especially at high temperatures, for example, in summer, they are detrimental to the skin.

On the other hand, silicone oil has recently come to be used as an oil for applying deodorants to the skin. The major reason therefor is an improvement in the touch such as an increased slidability attributed to the extremely low intermolecular force of the silicone oil.

The silicone oil would be free from the above problem of preventing the cutaneous respiration and the evapotranspiration of steam as caused by, for example, waxes because of its high permeabilities to gases and steam. However, the silicone oil has such a low surface tension that it is likely to diffuse on the skin with the result that no persistent film can be formed for the active ingredients. The use of siloxanes is disclosed in JP-A 5-255056.

Polysiloxanes having long-chain alkyl groups, as bases capable of forming films on the skin are applied, in skin care preparations. These utilize the crystallinity of the alkyl groups, and a mixture of a plurality of polysiloxanes functions while a polysiloxane having alkyl groups at its both ends alone functions to inhibit the evapotranspiration of moisture from dry skin, these polysiloxanes are not only do they become oily and sticky to the touch near the body temperature because of their low melting points but also the durability of each of the films at high temperatures becomes poor. By contrast, the polysiloxane for use in the present invention effectively utilizes the high steam permeability of the silicone contrary to the above functions. And the polysiloxane does not prevent the evapotranspiration of moisture while it has the property of persistently holding the active ingredients on the skin. So, it can be advantageously used especially in a period of profuse sweating in summer.

DISCLOSURE OF THE INVENTION

Therefore, it is an object of the present invention to provide a porous particulate which is amphoteric and capable of adsorbing a large amount of an acid or a base stronger than the acid or basic groups thereof, and has an average particle size of 50 μm or less.

Another object of the present invention is to provide a cosmetic such as a deodorant which has a high deodorant effect and is excellent in immediacy and persistence.

Accordingly, the task of the present invention is to provide a deodorant excellent in the persistence of deodorant effect which forms a film capable of persistently holding active ingredients on the skin without preventing the cutaneous respiration and the evapotranspiration of steam when applied to the skin, thus being able to prevent the scattering and flow down of active ingredients.

As a result of the intensive studies, the present inventors have found an amphoteric porous particulate based on a basic polysaccharide as a natural material which has both anionic and cationic properties and which contains basic and acid group capable of reacting with strong acids and bases in polar or nonpolar solvents in amounts per particle strikingly greater than the case of the conventional particulates. Further, they have that the use of this amphoteric porous particulate leads to the exertion of deodorant performance of having extremely high acid capturing properties to thereby be free from the lowering of acidic substance capturing capability with the lapse of time. The present invention has been completed on the basis of these findings.

The present invention mainly provides a porous particulate having a deodorant effect, a process for producing the same, a cosmetic composition containing the same, a cosmetic composition containing a chitosan particulate as a deodorant and a cosmetic containing polysiloxane as an oil, especially a deodorant composition.

Specifically, first, the present invention provides an amphoteric porous particulate comprising a polymer of a basic polysaccharide and an organic acid containing a reactive vinyl group or a salt thereof and having an average particle size of 50 μm or less. It is preferred that the porous particulate be composed of spherical fine particles, that the specific surface area of the porous particulate be in the range of 10 to 300 m$^2$/g, that the basic polysaccharide be chitosan, and that the organic acid containing a reactive vinyl group or salt thereof be methacrylic acid or a salt thereof.

This particulate may be produced by emulsifying or suspending an aqueous solution containing a basic polysaccharide and an organic acid having a reactive vinyl group in a hydrophobic solvent and thereafter effecting polymerization thereof. It is preferred that, after the polymerization, a polymerization reaction mixture be dropped into or added at once to an organic solvent containing a base to thereby precipitate a porous particulate. The organic acid may be used in a molar amount of 0.1 to 500 times the number of moles of monosaccharide units composing the basic polysaccharide.

Moreover, the present invention provides a cosmetic composition containing the above amphoteric porous particulate preferably in an amount of 0.1 to 70% by weight and being useful as a deodorant.

The cosmetic composition may contain ingredients conventionally employed in cosmetic recipes. For example, it may contain an oil.

Also, the present invention contains an amphoteric porous particulate of spherical fine particles, which comprises a polymer of a basic polysaccharide and an organic acid containing a reactive vinyl group and having an average particle size of 50 μm or less.

Further, the present invention provides a chitosan particulate having an average particle size of 0.01 to 50 μm as a deodorant, a cosmetic composition, for example, a deodorant containing the same, and a method of deodorization using the same.

It is preferred that the chitosan particulate have a specific surface area of 10 to 300 m$^2$/g, that the chitosan particulate have an available amino group content of $1.0 \times 10^{-7}$ to $1.0 \times 10^{-2}$ mol/g, and that the chitosan particulate be composed of spherical fine particles.

Still further, the present invention provides a polysiloxane having long-chain alkyl groups and a melting point of 20° C. or above as the oil component for a cosmetic, especially a deodorant.

Still further, the present invention provides a composition containing the above polysiloxane in an amount of 0.01 to 99% by weight together with a basic substance or basic polysaccharide and the above porous particulate or chitosan as a deodorant.

It is preferred that the above polysiloxane have a melting point of 60° to 140° C., that the polysiloxane have long-chain alkyl groups at both its molecular terminals, and that the proportion of the sum total of the long-chain alkyl groups in the polysiloxane having long-chain alkyl groups be in the range of 0.5 to 40% by weight.

Now the present invention will be described in greater detail.

The amphoteric porous particulate of the present invention can be obtained by emulsifying or suspending an aqueous solution containing a basic polysaccharide and an organic acid having a reactive vinyl group in a hydrophobic solvent and thereafter effecting polymerization thereof.

The basic polysaccharide suitable for use in the present invention is a compound having such a structure that pyranose rings having primary or secondary amino groups are bonded through ether chains. Examples thereof include chitosan as a polyglucosamine, chitin as an acetylation product of chitosan, polygalactosamine, and an acetylation product thereof. Since a naturally occurring chitin generally contains, in part, free amino groups, i.e. non-acetylated groups, the chitin for use in the present invention has a degree of de-acetylation of less than 30%, while the chitosan for use in the present invention has a degree of de-acetylation of at least 30%. This basic polysaccharide includes ones partially modified by such reactions as acylation, etherification and esterification. The present invention is characterized by the formation of a porous structure, so that the use of chitosan is preferred. In the present invention, although the molecular weight of the basic polysaccharide is not particularly limited, ones having a molecular weight of about ten thousand to one million are generally employed.

A water-soluble organic acid capable of dissolving the basic polysaccharide to thereby provide an aqueous solution and having in its molecule at least one reactive vinyl group and at least one acid group may be mentioned as the organic acid having a reactive vinyl group suitable for use in the present invention. Examples thereof include unsaturated carboxylic acid monomers such as acrylic, methacrylic, crotonic, itaconic and maleic acids; unsaturated sulfonic acid monomers such as styrenesulfonic acid, 2-acrylamido-2-methylpropanesulfonic acid, 3-sulfopropyl (meth)acrylate and bis(3-sulfopropyl) itaconate; and unsaturated phosphoric acid monomers such as vinylphosphonic acid, vinyl phosphate, bis(methacryloxyethyl) phosphate, diphenyl-2-acryloyloxyethyl phosphate, diphenyl-2-methacryloyloxyethyl phosphate, dibutyl-2-acryloyloxyethyl phosphate, dibutyl-2-methacryloyloxyethyl phosphate and dioctyl-2-(meth)acryloyloxyethyl phosphate. These may be used either individually or in combination. Of these, unsaturated carboxylic acid monomers having relatively low acidities are preferred, and methacrylic acid giving a polymer having a low acidity is especially preferred. For obtaining the amphoteric porous particulate, the organic acid is used in a molar amount of 0.1 to 500 times, preferably 0.5 to 10 times the number of moles of monosaccharide units composing the basic polysaccharide. From the viewpoint that the characteristics of the individual polymers are fully exhibited, it is especially preferred that the organic acid be used in a molar amount of 1.0 to 5 times the number of moles of monosaccharide units.

The above organic acid having a reactive vinyl group may be arbitrarily mixed with various types of acids. Examples of the miscible acids include inorganic acids such as hydrochloric, sulfuric and phosphoric acids; and organic acids such as formic, acetic, lactic, citric, tartaric, succinic, malic, oxalic, glycolic, dichloroacetic and trifluoroacetic acids.

Further, copolymerization may be effected with the use of another monomer which is copolymerizable with the organic acid having a reactive vinyl group. For example, unsaturated acid esters, organic acid vinyl esters and aromatic vinyl monomers may be mentioned as such other copolymerizable monomers. Especially, water-soluble monomers which can be synthesized by the W/O type polymerization are preferred, examples of which include unsaturated acid esters such as 2-hydroxyethyl (meth)acrylate, 2-hydroxypropyl (meth)acrylate, ethylene glycol di(meth)acrylate, diethylene glycol di(meth)acrylate, triethylene glycol di(meth)acrylate, and polyethylene glycol di(meth)acrylate; organic acid vinyl esters such as vinyl acetate and vinyl propionate; and aromatic vinyls such as vinylpyridine. Further, a compound having a reactive group may be added to the reaction system, if it is capable of reacting with the acid group of the organic acid having a reactive vinyl group. Still further, a chain transfer agent and a terminator may be added to the reaction system.

In the present invention, the emulsion or suspension polymerization may be carried out in the presence or absence of a surfactant. It is preferred that the polymerization be effected in the presence of a surfactant. Conventional anionic, nonionic, cationic and amphoteric surfactants may be used in the present invention. For example, use is made of an anionic surfactant such as dodecyl sulfate, dodecyl benzenesulfonate or polyoxyethylene nonylphenyl ether sulfate; a cationic surfactant such as octadecyltrimethylammonium chloride; a nonionic surfactant such as polyoxyethylene dodecyl ether, polyoxyethylene cetyl ether, polyoxyethylene nonylphenyl ether, sorbitan monostearate, sorbitan monooleate, sorbitan monolaurate, polyoxyethylene sorbitan monostearate, polyoxyethylene sorbitan monooleate or polyoxyethylene sorbitan monolaurate; and an amphoteric surfactant such as alkyldimethylaminoacetic acid betaine, alkylamidodimethylaminoacetic acid betaine or 2-alkyl-N-carboxy-N-hydroxyimidazolinium betaine. The amphoteric ion is present in the particulate, so that nonionic surfactants are preferred from the viewpoint of the stability of the particles. The above surfactants may be used either individually or in combination.

Examples of the hydrophobic solvents for use in the reaction to be conducted in the present invention include hydrocarbons such as pentane, hexane, heptane, octane, nonane, decane and cyclohexane; aromatics such as toluene and benzene; ethers such as petroleum ether and diethyl ether; halogenated hydrocarbons such as chloroform and carbon tetrachloride; ketones such as acetone, methyl ethyl ketone and diethyl ketone; and long-chain alcohols such as hexanol and heptanol. In the present invention, it is preferred that the reaction be conducted in the above hydrophobic solvent after the above surfactant has been dissolved therein. The surfactant concentration of the hydrophobic solvent is preferred to be in the range of 0.1 to 10.0% by weight, especially 0.5 to 5.0% by weight.

In the present invention, further, use may be made of a water-soluble polymer which acts as an emulsifying agent or protective colloid and is effective in stabilizing the particles, such as hydroxyethylcellulose, polyvinyl alcohol, cationic polyvinyl alcohol having a quaternary salt group incorporated therein, anionic polyvinyl alcohol having a carboxylic acid or sulfonic acid group incorporated therein, starch or cationic starch having a quaternary salt group incorporated therein.

The polymerization initiator for use in the present invention is generally used water- or oil-soluble peroxodisulfates, peroxides and azobis compounds which undergo free-radical decomposition under heating or in the presence of a reducing substance to thereby initiate the addition polymerization of a monomer. For example, a peroxide such as potassium persulfate, ammonium persulfate, hydrogen peroxide or t-butyl hydroperoxide; or an azo compound such as 2,2'-azobis-2-amidinopropane salt (V-50) or 4,4'-azobis-4-cyanopentanoic acid may be used as the initiator. If desirable, the initiator may be combined with a reducing agent to use the same as a redox initiator. The above polymerization initiators may be used either individually or in combination. The polymerization initiator may be added to an acidic aqueous solution of an organic acid of a basic polysaccharide. Alternatively, it may directly be added to an emulsion system. The polymerization initiator may be used in an amount of 0.05 to 10.0% by weight based on the organic acid.

In addition to the above monomers, surfactant and polymerization initiator, if desired, a chain transfer agent such as a mercaptan compound and a pH buffer such as sodium carbonate may be used in the polymerization according to the present invention.

In the process of the present invention, first, an acidic aqueous solution of an organic acid of a basic polysaccharide is mixed with a hydrophobic solvent to which a surfactant has been added, followed by mechanical agitation with the use of an emulsifier to thereby effect emulsification. Thus, a W/O emulsion is prepared. A homogenizer, a high-pressure homogenizer, a milder, a homomixer, an ultrasonic emulsifier, a nanomizer system or a glass membrane-emulsifier may be used as the emulsifier.

Alternatively, according to the customary reversed-phase suspension technique, a W/O suspension may be prepared from an acidic aqueous solution of an organic acid of a basic polysaccharide and a hydrophobic solvent to which a surfactant has been added, which suspension is directly subjected to polymerization reaction.

The mixing ratio of the acidic aqueous solution of an organic acid of a basic polysaccharide to the hydrophobic solvent at the time of emulsification/suspension may be freely selected as long as it is within the range of 70/30 to 0.1/99.9 on the volume basis.

In the present invention, a polymerization initiator is added to the prepared W/O emulsion or suspension of a basic polysaccharide, and polymerization is effected at 20° to 80° C. The polymerization is completed within a period of 0.1 to 24 hours. The resultant mixture is cooled and dropped into or added at once to an organic solvent to thereby precipitate a porous particulate.

The obtained particulate is treated by filtration, centrifugation or the like to thereby separate a solid from a liquid. The solid is repetitively washed with an alcohol or the like and dried, thereby obtaining a powdery particulate.

Examples of the organic solvents preferably employed herein include alcohols such as methanol, ethanol, propanol, isopropanol, butanol, hexanol, heptanol and octanol; polar solvents such as acetone, acetonitrile, tetrahydrofuran, dioxane and ethyl acetate; and nonpolar solvents such as cyclohexane, hexane, heptane and octane.

It is preferred that a base be added to the organic solvent. Examples of the bases suitably added include amines such as ammonia, methylamine, ethylamine, propylamine, butylamine, isobutylamine, hexylamine, octylamine, amino-modified silicone, ethylenediamine, propylenediamine and butylenediamine; and alkaline substances such as sodium hydroxide, potassium hydroxide, calcium hydroxide, sodium carbonate, sodium alkoxides and potassium alkoxides. The base is added in an amount of preferably 0.1 to 2.0 mol. %, still preferably 0.8 to 1.2 mol. % based on the organic acid polymer of the particulate.

The porous particulate may include in its body an inorganic substance such as ZnO or MgO, a basic substance such as arginine, a lipophilic substance such as cyclic silicone, triglyceride or squalene, and a perfume.

The amphoteric porous particulate of the present invention has an average particle size of 50 μm or less. The average particle size is generally at least 0.01 μm and preferably ranges from 0.1 to 30 μm. When the average particle size is greater than 50 μm, the amount of the basic and acid group capable of reacting with strong acids and bases per particle is so reduced as to lower the adsorptive effect of the particulate.

Herein, the average particle size is one determined by measuring a 1% by weight ethanol solution of the polymer particulate at room temperature by the use of a laser diffraction particle size distribution meter (LA-100 manufactured by Horiba).

Although the configuration of the amphoteric porous particulate of the present invention is not particularly limited; it is preferred that the particulate be composed of spherical particles from the viewpoint that the feel is excellent at the application of the particulate to the skin.

The amphoteric porous particulate of the present invention has a specific surface area of 10 to 300 $m^2/g$. For ensuring a satisfactory adsorptive effect for acids and bases, it is preferred that the specific surface area range from 20 to 200 $m^2/g$, especially from 25 to 150 $m^2/g$.

Herein, the specific surface area is one determined in accordance with the BET one-point method by the use of an automatic flow-type specific surface area meter (Flow Sorb model 2300 manufactured by Shimadzu Corp.). A large specific surface area means that the particulate is porous.

The chitosan particulate suitable for use in the present invention may be prepared by heating chitin as a substance constituting the mantle of a crustacean such as a lobster, a crab or an insect in a 30 to 50% by weight aqueous alkali solution at 60° C. or higher to thereby effect de-acetylation and atomizing the obtained chitosan particulate by a given method.

Various methods are available for atomizing the chitosan, which include, for example, a method (1) in which an acidic aqueous solution of chitosan is dropped into an aqueous alkali solution through a nozzle, a method (2) in which an acidic aqueous solution of chitosan is formed and sprayed into a high-temperature atmosphere and dried, and a method (3) in which an acidic aqueous solution of chitosan is mixed with a hydrophobic solvent and emulsified to thereby form an emulsion, which is poured into a base or an organic solvent to thereby coagulate the chitosan (emulsification process). Of these, the method (3) is preferred because a chitosan particulate whose available amino group content and specific surface area are large and which has a regulated configuration can be obtained.

With respect to the configuration of the chitosan particulate, the particulate may be composed of particles each of which is spherical, amorphous or nonspherical but having a definite shape. A chitosan particulate composed of spherical particles is preferred because an excellent feel is provided at the time of application to the skin. As used herein, the term "nonspherical but having a definite shape" refers to a shape having an uneven structure obtained by shrinkage and deformation of a ball. For example, it means not spherical but definite shape such as a red blood cell, cap or golf ball shape.

The cap shape is obtained by monoaxial mono-directional shrinkage and deformation of a hollow ball, while the red blood cell shape is obtained by monoaxial bidirectional shrinkage thereof. Multiaxial multidirectional shrinkage and deformation of a hollow ball gives a tridirectionally uneven shape or a golf ball shape.

The procedure for obtaining a chitosan particulate which is spherical or nonspherical but having a definite shape according to the above method (3), i.e., the emulsification process will now be described.

In the preparation of an acidic aqueous solution of chitosan, an acid for use in such an acidic aqueous solution may be inorganic acids such as hydrochloric, sulfuric and phosphoric acids; and organic acids such as formic, acetic, lactic, citric, tartaric, succinic, malic, oxalic, glycolic, dichloroacetic and trifluoroacetic acids. Of these, tartaric, succinic, malic and glycolic acids are preferred from the viewpoint of solubility, stability and smell. Also, a water-soluble organic acid having in its molecule a reactive vinyl group, especially at least one reactive vinyl group, may be used in the above acidic aqueous solution. Examples of the above water-soluble organic acids include unsaturated carboxylic acid monomers such as acrylic, methacrylic, crotonic, itaconic and maleic acids; unsaturated sulfonic acid monomers such as styrenesulfonic acid, 2-acrylamido-2-methylpropanesulfonic acid, 3-sulfopropyl (meth)acrylate and bis-(3-sulfopropyl)-itaconate; and unsaturated phosphoric acid monomers such as vinylphosphonic acid, vinyl phosphate, bis-(methacryloxyethyl) phosphate, diphenyl-2-acryloyloxyethyl phosphate, diphenyl-2-methacryloyloxyethyl phosphate, dibutyl-2-acryloyloxyethyl phosphate, dibutyl-2-methacryloyloxyethyl phosphate and dioctyl-2-(meth) acryloyloxyethyl phosphate. These may be used either individually or in combination. Of these, methacrylic acid giving a polymer having a low acidity is especially preferred.

The acidic aqueous solution of chitosan is generally prepared by gradually adding chitosan to an aqueous solution of the above acid heated at 50 to 70° C. while stirring to thereby dissolve the chitosan. In this step, the acid concentration of the aqueous solution is not particularly limited as long as chitosan is soluble therein. Although the chitosan concentration is also not particularly limited, 1 to 10% by weight is preferred from the viewpoint of the viscosity.

In the present preparation, a nonionic surfactant is preferably employed as the emulsifying agent in the emulsification. Examples of the suitable nonionic surfactants include sorbitan monostearate, sorbitan monooleate, sorbitan monolaurate, polyoxyethylene sorbitan monostearate, polyoxyethylene sorbitan monooleate, polyoxyethylene sorbitan monolaurate, polyoxyethylene lauryl alcohol ether and polyoxyethylene cetyl alcohol ether. These emulsifying agents may be used either individually or in combination.

The hydrophobic solvent to be employed for dissolving the above emulsifying agent may be selected from among, for example, hydrocarbons such as hexane and cyclohexane; aromatics such as toluene and benzene; ethers such as petroleum ether and diethyl ether; and halogenated hydrocarbons such as chloroform and carbon tetrachloride. The emulsifying agent concentration of the hydrophobic solvent is suitable to be in the range of 0.1 to 10.0% by weight, preferably 0.5 to 5.0% by weight.

In the present preparation, a W/O emulsion of an acidic aqueous solution of chitosan is produced by adding a hydrophobic solvent containing an emulsifying agent to an acidic aqueous solution of chitosan and by conducting mechanical agitation with the use of an emulsifier to thereby effect emulsification. A homogenizer, a high pressure homogenizer, a milder, a homomixer, a touch mixer, an ultrasonic emulsifier, a nanomizer system or a glass-membrane emulsifier may be used as the emulsifier.

In the emulsification, the mixing ratio of the acidic aqueous solution of chitosan to the hydrophobic solvent containing an emulsifying agent is preferred to range from 9/1 to 1/9, especially from 7/3 to 3/7 on the volume basis.

In the present preparation of the chitosan particulate, one composed of spherical particles may be obtained by pouring the above-prepared W/O emulsion of an acidic aqueous solution of chitosan in an organic solvent per se or an organic solvent containing a base to thereby coagulate and precipitate the chitosan while maintaining the spherical shape thereof.

When an organic solvent per se is employed in the coagulation and precipitation of a chitosan emulsion, it is preferably used alcohols such as methanol, ethanol, propanol, isopropanol, butanol and octanol; polar solvents such as acetone, acetonitrile, tetrahydrofuran, dioxane and ethyl acetate; and nonpolar solvents such as cyclohexane and hexane.

When the coagulation is an organic solvent containing a base, the organic solvent is preferably used alcohols such as methanol, ethanol, propanol, isopropanol and butanol; polar solvents such as acetone, acetonitrile, tetrahydrofuran, dioxane and ethyl acetate; and nonpolar solvents such as cyclohexane and hexane. Of these, alcohols having 4 or less carbon atoms and polar solvents such as acetone, acetonitrile, tetrahydrofuran, dioxane and ethyl acetate are preferred. Examples of the suitable bases include amines such as ammonia, methylamine, ethylamine, propylamine, butylamine, isobutylamine, hexylamine, octylamine, amino-modified silicone, ethylenediamine, propylenediamine and butylenediamine; and alkaline substances such as sodium hydroxide, potassium hydroxide and calcium hydroxide. Of these, sodium hydroxide, potassium hydroxide, butylamine, hexylamine and octylamine are preferred. Further, butylamine, hexylamine and octylamine are especially preferred because a chitosan particulate composed of particles having an increased sphericity can be obtained.

Although the amount of the coagulation fluid depends on the type of the coagulation fluid, it is generally 2 to 50 times the volume of the emulsion.

When a W/O emulsion containing chitosan is dropped into the above coagulation fluid under agitation, the chitosan is coagulated and precipitated in the form of spherical particles. The spherical particles of chitosan are collected by filtration or centrifugation, satisfactorily washed with an alcohol or the like, and dried. Thus, a chitosan particulate composed of spherical particles is obtained.

In the present preparation, one composed of particles each being nonspherical but having a definite shape may be obtained by employing a solution of a mixture of an amine and an alcohol as the above coagulation fluid. Examples of the suitable amines include ammonia; primary amines each having an alkyl chain of about 1 to 12 carbon atoms; secondary amines such as diethylamine, diisobutylamine and diisopropylamine; tertiary amines such as triethylamine and tri-n-octylamine; diamines such as ethylenediamine, propylenediamine and butylenediamine; amino alcohols such as monoethanolamine, diethanolamine and triethanolamine; heterocyclic amines such as pyridine and pyrrole; and polyethyleneimine, amino-modified acrylic polymer and amino-modified silicone.

Of the above amines, amines which are not completely miscible with water and rather only slightly soluble in water can be suitably employed. Thus, it is preferred to employ amines each having an alkyl group of 2 to 12 carbon atoms, especially monoalkylamines or primary amines each having an alkyl group of 4 to 12 carbon atoms, secondary amines each having an alkyl group of 3 to 10 carbon atoms, tertiary amines each having an alkyl group of 2 to 8 carbon atoms and amino-modified silicone, still especially amino-modified silicone.

The alcohol suitable for use in the present preparation is, for example, a monoalcohol having an alkyl group of about 1 to 20 carbon atoms, of which a monoalcohol having an alkyl group of 4 to 12 carbon atoms such as butanol, isobutyl alcohol, hexanol, heptanol or octanol is preferred.

When the employed amine is amino-modified silicone, isobutyl alcohol and butanol are especially preferred. On the other hand, when the employed amine is a primary amine such as n-butylamine, a monoalcohol having 6 to 12 carbon atoms is especially preferred.

In the present preparation, although the mixing ratio of the amine to the alcohol in the solution of a mixture of an amine and an alcohol is not particularly limited, it is preferred to range from 2/3 to 8/2 on the volume basis when amino-modified silicone is used as the amine. When the volume ratio exceeds 8/2, the configuration of the resultant particulate is an agglomerate of fine particles each being nonspherical but having a definite shape, so that dispersed particles cannot be obtained. On the other hand, when the volume ratio is less than 2/3, the resultant particulate is composed of spherical particles although dispersed fine particles are obtained, so that fine particles each nonspherical but having a definite shape cannot be obtained.

In the present preparation, the coagulation temperature is not particularly limited as long as it is not higher than the boiling points of the coagulation fluid and the hydrophobic solvent and water of the emulsion. However, the configuration of the particulate can be regulated by the coagulation temperature. Although depending on the type of the solution of a mixture of an amine and an alcohol, generally, the coagulation temperature at 20° to 50° C. produces particles each in tridirectionally uneven definite form while at 50° C. or higher produces particles each in red-blood-cell-shaped or cap-shaped definite form. The coagulation fluid is generally employed in an amount of 2 to 50 times the volume of the emulsion although it depends on the type of the coagulation fluid, etc.

Dropping of the W/O emulsion of an acidic aqueous solution of chitosan into the above coagulation fluid while stirring leads to coagulation and precipitation of chitosan in the form of particles each being nonspherical but having a definite shape. The chitosan particles being nonspherical but having definate shape are separated by the conventional method such as filtration or centrifugation, satisfactorily washed with, for example, an alcohol, and dried. Thus, a chitosan particulate composed of particles each being nonspherical but having a definite shape which has an average particle size of less than 50 μm is obtained.

The chitosan particulate to be used herein includes various forms of chitosan particulates such as a chitosan particulate having undergone a chemical modification such as partial acetylation, a crosslinked chitosan particulate obtained by crosslinking with an epoxy group and the like, a coated chitosan particulate obtained, for example, by emulsion polymerization with the use of chitosan as protective colloid, a composite chitosan particulate obtained by combination with organic or inorganic powder, and a chitosan/vinyl polymer composite particulate obtained by reversed-phase suspension polymerization.

The chitosan particulate of the present invention has an average particle size of 0.01 to 50 μm, preferably 0.1 to 30 μm and still preferably 1 to 30 μm. When the average particle size is greater than 50 μm, rough touch results in the application thereof to the skin to thereby give bad feel. On the other hand, when the average particle size is less than 0.01 μm, unfavorably, the blending becomes difficult and creaky touch results in the application thereof to the skin. Herein, the average particle size is one determined by measuring a 1% by weight ethanol solution of the chitosan particulate at room temperature by the use of a laser diffraction particle size distribution meter (LA-100 manufactured by Horiba).

It is preferred that the chitosan particulate of the present invention have an available amino group content of $1.0 \times 10^{-7}$ to $1.0 \times 10^{-2}$ mol/g, especially $1.0 \times 10^{-5}$ to $1.0 \times 10^{-2}$ mol/g, from the viewpoint that a satisfactory deodorant effect is attained. The term "available amino group content of the chitosan particulate (mol/g)" as used herein refers to the number of moles of the amino groups capable of forming salts with carboxylic acids per unit weight of the chitosan particulate. The available amino group content is one determined by adding a $2 \times 10^{-4}$ mol/l cyclohexane or ethanol solution of 4-phenylbutyric acid to a chitosan particulate, filtering the mixture through a membrane filter, and conducting UV spectrophotometry ($\lambda_{max}$=210 nm) of the filtrate.

The specific surface area of the chitosan particulate of the present invention is preferred to range from 10 to 300 m²/g, especially from 30 to 300 m²/g, and still especially 50 to 300 m²/g from the viewpoint that a satisfactory deodorant effect is attained. Herein, the specific surface area is one determined in accordance with the BET one-point method by the use of an automatic flow-type specific surface area meter (Flow Sorb model 2300 manufactured by Shimadzu Corp.). A large specific surface area means that the particulate is porous.

From the viewpoint of the strength of the particulate, it is preferred that the chitosan particulate of the present invention have a weight-average molecular weight of $1 \times 10^3$ to $1 \times 10^6$. This molecular weight is one determined by GPC with the use of a 0.5M acetate buffer (0.5M acetic acid+ 0.5M sodium acetate) as an eluent in a water-base column. The molecular weight is one calculated in terms of PEG.

The degree of de-acetylation of the chitosan particulate of the present invention is preferred to be at least 80% from the viewpoint that a satisfactory deodorant effect is attained. Herein, the degree of de-acetylation is one determined by colloid titration in which an acidic aqueous solution of chitosan is titrated with potassium polyvinylsulfate with the use of toluidine blue as the indicator. Another method may be employed in which 8-anilino-1-naphthalenesulfonate is used as the indicator so as to form a chitosan-indicator complex, followed by fluorometry.

The polysiloxane for use in the present invention has long-chain alkyl groups as the side chains or at both its molecular terminals. The number of carbon atoms and the molecular weight of each of the alkyl chains are not particularly limited as long as the melting point of the polysiloxane is 20° C. or above. When the melting point is lower than 20° C., it is melted by the skin temperature in the application to the skin, thereby becoming oily, likely to flow down and sticky and having a less tendency to remain on the skin, so that the active ingredients of the deodorant cannot be persistently held on the skin.

In the present invention, the long-chain alkyl group means an alkyl group whose average number of carbon atoms is at least 16. The average number of carbon atoms is preferably at least 30, still preferably in the range of 40 to 70.

The polysiloxane especially preferred in the present invention has a melting point of 60° to 140° C., contains long-chain alkyl groups at both its molecular terminals, and has a structure represented by the following general formula (I).

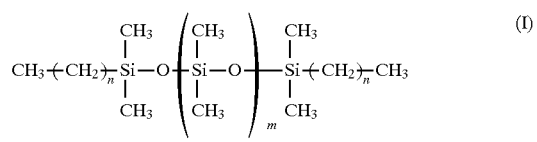

(wherein n is the average number of carbon atoms of the long-chain alkyl groups, satisfying the relationship: (n+1)

≧30; and m is a number of 0 or above, although not particularly limited, preferably ranges from 100 to 5000, because when it is 100 or above, the coating film has excellent moisture permeability and flexibility. The blendability of the compound is good in view of viscosity of 5,000 or less. From the same viewpoint, m is especially preferred to range from 200 to 5000)

The polysiloxane for use in the present invention can be produced by reacting a 1-olefin with polydimethylsiloxane having silicon-hydrogen bonds in the presence of a catalyst such as platinum. However, it is difficult to obtain a long-chain-alkyl-modified polydimethylsiloxane having a high melting point by the synthesis of the polysiloxane represented by the above general formula (I) and having long-chain alkyl groups at both its molecular terminals according to the above synthetic method. That is, although the polysiloxane represented by the above general formula (I) and having long-chain alkyl groups at both its molecular terminals may be obtained by reacting a 1-olefin with a polysiloxane having hydrogen atoms at both its molecular terminals as the starting material in the presence of a catalyst such as platinum, the molecular weight of the 1-olefin as the starting material is limited, so that it is difficult to obtain a long-chain-alkyl-modified polydimethylsiloxane having a melting point as high as, for example, 60° C. or above. Further, if a 1-olefin of high molecular weight is employed, it is difficult to remove remaining 1-olefin and catalyst. Therefore, the above synthetic method is not preferable. It is preferred that the polysiloxane represented by the above general formula (I) and having long-chain alkyl groups at both its molecular terminals be synthesized by the long-chain-alkyl-modified polysiloxane synthesizing process discovered by the inventors and disclosed in the specification of Japanese Patent Application No. 69478/1994. More specifically, a living polyethylene obtained by the living polymerization of ethylene is reacted with a cyclic siloxane, followed by the polymerization of a cyclic polydimethylsiloxane, a chain polydimethylsiloxane having a silanol group at its terminal or a mixture thereof in the presence of a catalyst. Thus, polydimethylsiloxane having long-chain alkyl groups at both its molecular terminals can be synthesized at a high reproducibility.

The synthesized polysiloxane having long-chain alkyl groups at both its molecular terminals can stand the flow down during a high-temperature season and fix the active ingredients of the deodorant on the skin for a prolonged period of time by virtue of the presence of crystalline alkyl groups of high melting point at both its molecular terminals. Further, the polysiloxane has such characteristics that, since the long-chain alkyl groups are present only at both the terminals, a siloxane portion ensuring high permeabilities to gases and steam is secured in the molecule at a high ratio, so that the cutaneous respiration and skin drying are not blocked. Therefore, the above polysiloxane having long-chain alkyl groups only at both its molecular terminals is especially preferred in the present invention.

The cosmetic of the present invention contains the amphoteric porous particulate obtained by the above processes. The content of the amphoteric porous particulate in the cosmetic of the present invention is preferred to range from 0.1 to 70% by weight, especially from 10 to 60% by weight from the viewpoint of the deodorant effect and blend stability.

In the present invention, the cosmetic comprehends skin cosmetics such as antiperspirants, deodorants, packs and humectants, and hair care products. It is preferred that the composition of the present invention be used as a deodorant.

In the use as a deodorant, ingredients arbitrarily selected from among the conventional ones may be added to the cosmetic of the present invention. Examples of such ingredients include metallic oxides such as zinc and magnesium oxides; antiperspirant astringent agents such as aluminum hydroxychloride and zinc sulfocarbolate; bactericides such as isopropylmethylphenol, trichlorocarbanilide and Sanisol; platy and spherical powders such as talc, Amihope and nylon powder; solid and semisolid oils such as vaseline, ceresin, higher fatty acids and higher alcohols; fluid oils such as squalane, ester oil, diglyceride and silicone oil; water-soluble polymers such as sodium polyacrylate, polyvinyl alcohol and methylcellulose; organic acids such as lactic and succinic acids; humectants such as glycerol and sorbitol; antiphlogistics such as dipotassium glycyrrhizinate and allantoin; and thickeners, surfactants, coloring matters, perfumes, and refrigerants. These can be freely added as long as the addition is not detrimental to the objects of the present invention. In particular, it is preferred that an oil capable of dispersing the amphoteric porous particulate be contained in the deodorant, and that the oil content of the deodorant range from 10 to 90% by weight.

The form in which the cosmetic of the present invention is used is not particularly limited. For example, it is used in the form of lotion, aerosol, powder, stick, cream, pack, soap or shampoo.

From the viewpoint of deodorant effect and blend stability, the content of the chitosan particulate in the deodorant of the present invention is preferred to range from 0.1 to 50% by weight, especially from 10 to 50% by weight, and still especially from 20 to 50% by weight.

Ingredients arbitrarily selected from among the conventional ones may be added to the deodorant of the present invention. Examples of such ingredients include metallic oxides such as zinc and magnesium oxides; antiperspirants such as aluminum hydroxychloride and tannic acid; bactericides such as trichlorohydroxydiphenyl ether (triclosan), isopropylmethylphenol, trichlorocarbanilide and Sanisol; and masking agents such as perfumes. Further, ingredients which may be added to the deodorant of the present invention include oils such as dimethylsiloxane, silicone oils (e.g., volatile cyclic silicone), higher fatty acid esters, wax and higher alcohols (e.g., stearyl alcohol); humectants such as glycerol and sorbitol; surfactants such as metallic soaps (e.g., sodium stearate) and nonionic surfactants (e.g., sorbitan fatty acid ester); antiseptics such as methylparaben, butylparaben and propylparaben; powder such as nylon powder and talc; antiphlogistics such as dipotassium glycyrrhizinate, allantoin and guaiazulene; thickeners such as polysodium acrylate, polyvinyl alcohol, methylcellulose, bentonite and hectorite; coloring matters such as Green No. 3, Blue No. 1, Yellow No. 4 and Yellow No. 5; and astringent agents.

The form in which the deodorant of the present invention is used is not particularly limited. For example, it is used in the form of lotion, aerosol, powder, stick or cream.

It is preferred that the proportion of the long-chain alkyl portions of the polysiloxane having long-chain alkyl groups and a melting point of 20° C. or higher for use in the present invention be in the range of 0.5 to 40% by weight, especially 1 to 40% by weight. When this proportion exceeds 40% by weight, the resultant film would have degraded moisture permeability and flexibility. On the other hand, when the proportion is less than 0.5% by weight, the film would easily flow down by sebum or the like, would be sticky, and would have difficulty in remaining on the skin especially at high temperatures.

The polysiloxane having long-chain alkyl groups and a melting point of 20° C. or higher is blended in the deodorant of the present invention in an amount of 0.01 to 99% by weight, preferably 1 to 70% by weight, although it depends on the use and blend forms. When the amount is less than 0.01% by weight, the active ingredients of the deodorant cannot persistently be held on the skin, so that the deodorant effect cannot be persistent. On the other hand, when the amount exceeds 99% by weight, the amount of blended active ingredients becomes so small that it would become difficult to attain desirable deodorant effect.

Ingredients arbitrarily selected from among the conventional one may be added to the above deodorant of the present invention, and the deodorant effect can be retained for a prolonged period of time even under such harsh conditions as high temperatures and sweating by persistently holding the ingredients on the skin. Examples of such added ingredients include astringent agents such as aluminum hydroxychloride and zinc phenolsulfonate; bactericides such as isopropylmethylphenol, trichlorocarbanilide and Sanisol; and powders such as talc, Amihope and nylon powder.

The deodorant of the present invention is endowed with a high deodorant effect by adding a basic substance to the same to thereby capture the organic acids causing body smells in the coating film. Examples of such basic substances include inorganic materials, for example, metallic oxides such as zinc and magnesium oxides and organic compounds having an amino group, such as chitosan. The content of the basic substance in the deodorant of the present invention is preferred to be about 0.1 to 70% by weight from the viewpoint of deodorant effect and blend stability.

It is preferred that the porous particulate described hereinbefore as the above basic substance be blended in the deodorant of the present invention, because a high deodorant effect can be retained for an extremely prolonged period of time. Although the mechanism has not yet been elucidated, it is believed that the amphoteric porous particulate is dispersed in a flexible and hydrophobic film composed of the modified polysiloxane having long-chain alkyl groups and a melting point of 20° C. or higher, and that oily organic acids are diffused into the film with the result that these are captured by the amphoteric porous particulate. This hydrophobic film is resistant to sweat and moisture from outside and has high moisture permeability, so that a very excellent deodorant effect can be exerted especially in the application to regions consistently in an environment of high temperature and humidity, such as the axilla, foot, scruff of the neck and chest, or in the use during summertime swimming and other sports.

The above amphoteric porous particulate is obtained by emulsifying or suspending an aqueous solution containing a basic polysaccharide having an amino group, such as chitosan, and an organic acid monomer having a reactive vinyl group, such as methacrylic acid, in a hydrophobic solvent and effecting polymerization thereof.

The content of the amphoteric porous particulate in the deodorant of the present invention is preferred to be about 0.1 to 70% by weight from the viewpoint of deodorant effect and blend stability.

Although other ingredients such as a surfactant, an alcohol, water and oil materials may be added to the above deodorant of the present invention, the amount and method of addition are determined so as not to be detrimental to the effects of the present invention.

Although the above deodorant of the present invention may be obtained by mixing and agitating the polysiloxane having long-chain alkyl groups and a melting point of 20° C. or higher and other ingredients, occasionally, it may be needed to effect heating and melting.

The above deodorant of the present invention may be used in the form of stick, spray, mist spray, roll-on, cream or milky lotion.

[EFFECT OF THE INVENTION]

The porous particulate of the present invention is weakly acidic and weakly basic, thus being amphoteric. It is one obtained by internally crosslinking a basic polysaccharide with an acidic polymer. It has the capability of readily reacting with strong bases or acids in nonpolar and polar solvents to thereby capture the bases or acids in the porous particulate. Further, the porous particulate can retain its particulate form without being dissolved in various solvents having mutually different polarities. Still further, the porous particulate of the present invention based on a natural material is excellent in safety because no crosslinking agents are employed, so that it finds applications not only in the field of cosmetics and perfumes, e.g., skin cosmetics (antiperspirants, deodorants, packs and humectants) and hair care products, but also in drugs. Moreover, it is useful in fiber treatments, paper coatings, cement additives, covering materials, bactericides/bacteriostats, and agricultural chemicals.

[EXAMPLES]

Figure 1:
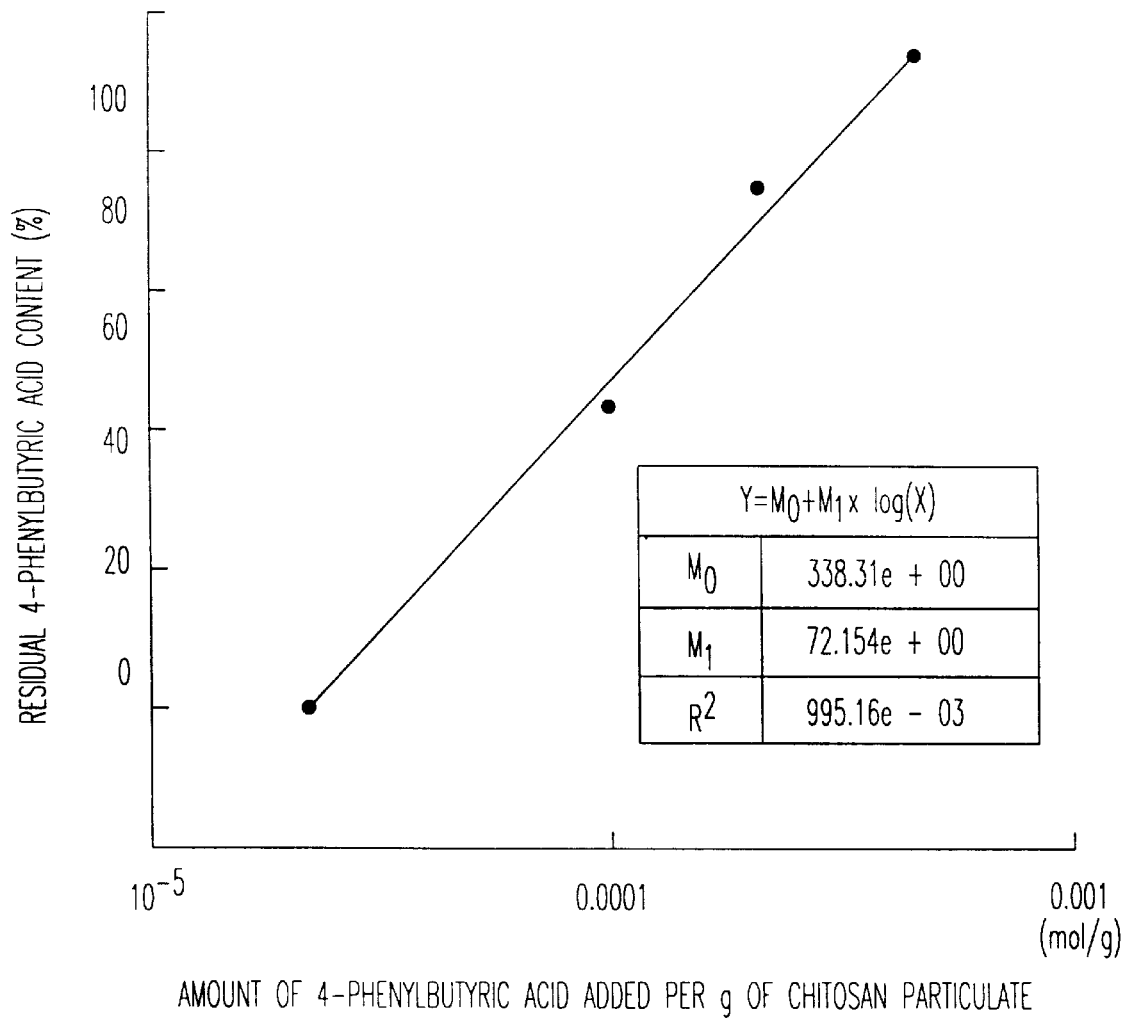
FIG. 1 is a graph in which the residual 4-phenylbutyric acid content (Y) is logarithmically plotted against the amount of 4-phenylbutyric acid added per gram of chitosan particulate (X) for calculating the available amino group content of the chitosan particulate obtained in Synthetic Example 1.

The present invention will now be described in greater detail with reference to the following Examples in which amphoteric porous particulates are produced and Formulation Examples in which deodorants are prepared, which should not be construed as limiting the scope of the invention.

Therein, percentage is given on the weight basis unless otherwise specified.

Example 1

Water was added to 80 g of commercially available chitosan (SK-10 produced by Koyo Chemical Co., Ltd., degree of de-acetylation: 85–88%, weight-average molecular weight: 130,000) until the total weight amounted to 900 g. 34.6 g of methacrylic acid (equimolar to the monosaccharide units of the chitosan) was added and dissolved while stirring at 60° C., thereby preparing an aqueous solution of chitosan and methacrylic acid. A solution obtained by dissolving 3 g of potassium persulfate in 100 g of ion-exchanged water was added to the above aqueous solution and agitated at room temperature for a few minutes.

The resultant chitosan solution was mixed with a 1.0% by weight cyclohexane solution of sorbitan monolaurate in a ratio of 5:5 (volumetric ratio) and agitated at a great rate of 15,000 rpm by means of a homogenizer, thereby obtaining a W/O emulsion.

A polymerization reaction was effected at 70° C. for two hours, and the reaction mixture was cooled to room temperature and dropped into ethanol in an amount of 5 times as many moles (by volume) under agitation. Agitation was continued for 30 min, and any agglomerate was removed by decantation. Immersion in ethanol and agitation followed by filtration through a Buchner funnel were conducted thrice. Then, vacuum drying was effected, thereby obtaining a particulate. The particle size and configuration of the obtained particulate are summarized and shown in Table 1.

Example 2

A particulate was obtained in the same manner as in Example 1, except that 69.3 g of methacrylic acid (2 times the number of moles of the monosaccharide units of the chitosan) was used in place of 34.6 g of methacrylic acid. The particle size and configuration of the obtained particulate arc summarized and shown in Table 1.

Example 3

A particulate was obtained in the same manner as in Example 1, except that 51.9 g of methacrylic acid (1.5 times the number of moles of the monosaccharide units of the chitosan) was used in place of 34.6 g of methacrylic acid. The particle size and configuration of the obtained particulate are shown in Table 1.

Example 4

A particulate was obtained in the same manner as in Example 1, except that 26.0 g of methacrylic acid (0.75 time the number of moles of the monosaccharide units of the chitosan) was used in place of 34.6 g of methacrylic acid. The particle size and configuration of the obtained particulate are summarized and shown in Table 1.

Example 5

A particulate was obtained in the same manner as in Example 1, except that 26.0 g of methacrylic acid (0.75 time the number of moles of the monosaccharide units of the chitosan) and 6 g of acetic acid (0.25 time the number of moles of the monosaccharide units of the chitosan) was used in place of 34.6 g of methacrylic acid. The particle size and configuration of the obtained particulate are summarized and shown in Table 1.

Example 6

A particulate was obtained in the same manner as in Example 1, except that 80 g of polygalactosamine (weight average molecular weight: 200,000) was used in place of chitosan. The particle size and configuration of the obtained particulate are summarized and shown in Table 1.

Example 7

A particulate was obtained in the same manner as in Example 1, except that a 5.0% by weight cyclohexane solution of sorbitan monolaurate was used in place of the 1.0% by weight cyclohexane solution of sorbitan monolaurate. The particle size and configuration of the obtained particulate are summarized and shown in Table 1.

Example 8

A particulate was obtained in the same manner as in Example 1, except that acrylic acid was used in place of methacrylic acid in an amount equimolar to the monosaccharide units of the chitosan. The particle size and configuration of the obtained particulate are summarized and shown in Table 1.

Example 9

A polymerization reaction was effected at 70° C. for 3 hours in the same manner as in Example 4. Thereafter, the reaction mixture was cooled to room temperature and neutralized with a solution of 0.05N (normality) aqueous NaOH/isopropanol (1/5 vol/vol) to a final pH of 9.0. Washing with isopropanol followed by filtration was conducted thrice, and vacuum drying was effected, thereby obtaining a particulate. The particle size and configuration of the obtained particulate are summarized and shown in Table 1.

Comparative Example 1

Water was added to 80 g of commercially available chitosan (SK-10 produced by Koyo Chemical Co., Ltd., degree of de-acetylation: 85–88%, weight-average molecular weight: 130,000) until the total weight amounted to 900 g. 34.6 g of methacrylic acid (equimolar to the monosaccharide units of the chitosan) was added and dissolved while stirring at 60° C., thereby preparing an aqueous solution of chitosan and methacrylic acid.

435 g of ion-exchanged water was added to 125 g of the above chitosan solution. 5.0% by weight of sorbitan monolaurate was added and mixed, and 0.73 g of potassium persulfate as a polymerization initiator was added. A polymerization reaction was effected at 70° C. for 5 hours, and the reaction mixture was cooled to room temperature, dropped into ethanol in an amount of 5 times as many moles (by volume) under agitation. Agitation was continued for 30 min, and any agglomerate was removed by decantation. Immersion in ethanol and agitation followed by filtration through a Buchner funnel were conducted thrice. Then, vacuum drying was effected, thereby obtaining particles. The particle size and configuration of the obtained particles are summarized and shown in Table 1.

Comparative Example 2

Particles were obtained in the same manner as in Comparative Example 1, except that acrylic acid was used in place of methacrylic acid in an amount equimolar to the monosaccharide units of the chitosan. The particle size and configuration of the obtained particles are summarized and shown in Table 1.

TABLE 1

| | Acidic aq. soln. of basic polysaccharide | | | | | | | Conc. | Form of particulate | | | |
|---|---|---|---|---|---|---|---|---|---|---|---|---|
| | | org. acid | | other mixed acid | | Hydro- | | of surfac- | | av. particle | sp. surface | |
| | basic poly- saccharide | type | amt. of addn.*1 | type | amt. of addn.*1 | phobic solvent | Sur- factant | tant (%) | form | size (μm) | area (m²/g) | Remark |
| Ex. | | | | | | | | | | | | |
| 1 | chitosan | methyacrylic acid | 1-fold mol | | | cyclo- hexane | sorbitan monolaurate | 1.00 | Perfectly spherical | 12 | 50 | reversed-phase suspension polymn. |
| 2 | chitosan | methacrylic acid | 2-fold mol | | | cyclo- hexane | sorbitan monolaurate | 1.00 | perfectly spherical | 14 | 55 | reversed-phase suspension polymn. |
| 3 | chitosan | methacrylic acid | 1.5-fold mol | | | cyclo- hexane | sorbitan monolaurate | 1.00 | perfectly spherical | 10 | 69 | reversed-phase suspension polymn. |
| 4 | chitosan | methacrylic acid | 0.75-fold mol | | | cyclo- hexane | sorbitan monolaurate | 1.00 | perfectly spherical | 8 | 72 | reversed-phase suspension polymn. |
| 5 | chitosan | methacrylic acid | 0.75-fold mol | acetic acid | 0.25- fold mol | cyclo- hexane | sorbitan monolaurate | 2.00 | perfectly spherical | 10 | 70 | reversed-phase suspension polymn. |
| 6 | poly- galactos- amine | methacrylic acid | 1-fold mol | | | cyclo- hexane | sorbitan monolaurate | 1.00 | perfectly spherical | 13 | 64 | reversed-phase suspension polymn. |
| 7 | chitosan | methacrylic acid | 1-fold mol | | | cyclo- hexane | sorbitan monolaurate | 5.00 | perfectly spherical | 13 | 63 | reversed-phase suspension polymn. |
| 8 | chitosan | acrylic acid | 1-fold mol | | | cyclo- hexane | sorbitan monolaurate | 1.00 | perfectly spherical | 8 | 60 | reversed-phase suspension polymn. |
| 9 | chitosan | methacrylic acid | 0.75-fold mol | | | cyclo- hexane | sorbitan monolaurate | 1.00 | perfectly spherical | 8 | 25 | reversed-phase suspension polymn. neutralization |
| Comp. Ex. | | | | | | | | | | | | |
| 1 | chitosan | methacrylic acid | 1-fold mol | | | aq. soln. | sorbitan monolaurate | 5.00 | amor- phous | 100 | 1 | aq. soln. polymn. |
| 2 | chitosan | acrylic acid | 1-fold mol | | | aq. soln. | sorbitan monolaurate | 5.00 | amor- phous | 100 | 2 | aq. soln. polymn. |

Note
*1 number of moles per monosaccharide unit of basic polysaccharide.

Now, formulation examples will be described below with respect to the deodorant containing the amphoteric porous particulate composed of spherical particles according to the present invention.

In the formulation examples described below, the deodorant effects were tested by the following method.

<Deodorant effect testing method>

Healthy males (aged 20 to 40) having strong axillary and foot smells were chosen and evaluated by organoleptic evaluations by four expert panelists. Specifically, first, the males having just arrived at office (around 9:00) had four expert panelists' organoleptic evaluations. Immediately after the evaluations, the deodorants prepared according to the following formulation examples were applied in appropriate amounts to the axillae and feet. Each male had the deodorant application at only one of the axillae and of the feet. The smells were evaluated just after the deodorant application and also in the evening before going home (around 16:00). None was applied to the other axilla and foot of each male to provide controls. The evaluations involved four expert panelists, grading into any of the following six grades, the average of which was determined with respect to the axillary smell in Formulation Examples 1 to 5 while with respect to the foot smell in Formulation Example 6. Moreover, the results of evaluation of the formulation containing zinc oxide (specific surface area: 50 m²/g) in place of the amphoteric porous particulate of the present invention are shown in the Comparative Formulation Example.

Criterion

0: not smells,

1: slightly smells,

2: smells though weakly,

3: definitely smells,

4: strongly smells, and

5: very strongly smells.

Formulation Example 1 deodorant lotion (ethanol base)

The deodorant lotion of the following composition was prepared and applied to the axillae to evaluate the deodorant effect thereof. The results are shown in Table 2.

| <Composition> | |
|---|---|
| amphoteric porous spherical particulate (Ex. 9) | 8.0% |
| amphoteric porous spherical particulate (Ex. 2) | 2.0% |
| glycerol | 5.0% |

-continued

| <Composition> | |
|---|---|
| water | 10.0% |
| ethanol | 75.0% |
| in total | 100.0% |

TABLE 2

| | | Evaluation | | |
|---|---|---|---|---|
| | | before appln. (ca 9:00) | just after appln. | before going home (ca 16:00) |
| Invention product | non-appln. part (control) | 5 | 5 | 5 |
| | appln. part | 5 | 2 | 3 |
| Comp. product (zinc oxide) | non-appln. part (control) | 5 | 5 | 5 |
| | appln. part | 5 | 4 | 4 |

Formulation Example 2 deodorant lotion (volatile silicon base)

The deodorant lotion of the following composition was prepared and applied to the axillae to evaluate the deodorant effect thereof. The results are shown in Table 3.

| <Composition> | |
|---|---|
| amphoteric porous spherical particulate (Ex. 9) | 50.0% |
| isopropyl myristate | 5.0% |
| dimethylsilicone | 5.0% |
| methylpolysiloxane | 40.0% |
| in total | 100.00% |

TABLE 3

| | | Evaluation | | |
|---|---|---|---|---|
| | | before appln. (ca 9:00) | just after appln. | before going home (ca 16:00) |
| Invention product | non-appln. part (control) | 5 | 5 | 5 |
| | appln. part | 5 | 1 | 3 |
| Comp. product (zinc oxide) | non-appln. part (control) | 5 | 5 | 5 |
| | appln. part | 5 | 4 | 4 |

Formulation Example 3 deodorant powder spray (liquid spray type)

The deodorant powder spray of the following composition was prepared and applied to the axillae to evaluate the deodorant effect thereof. The results are shown in Table 4.

| <Composition> | |
|---|---|
| Stock solution | |
| amphoteric porous spherical particulate (Ex. 9) | 40.0% |
| glycerol | 5.0% |
| isopropyl myristate | 5.0% |
| water | 5.0% |

-continued

| <Composition> | |
|---|---|
| ethanol | 45.0% |
| in total | 100.0% |
| Filling | |
| above stock solution | 35.0% |
| LPG gas | 65.0% |
| in total | 100.00% |

TABLE 4

| | | Evaluation | | |
|---|---|---|---|---|
| | | before appln. (ca 9:00) | just after appln. | before going home (ca 16:00) |
| Invention product | non-appln. part (control) | 5 | 5 | 5 |
| | appln. part | 5 | 1 | 3 |
| Comp. product (zinc oxide) | non-appln. part (control) | 5 | 5 | 5 |
| | appln. part | 5 | 4 | 4 |

Formulation Example 4 deodorant gel

The deodorant gel of the following composition was prepared and applied to the axillae to evaluate the deodorant effect thereof. The results are shown in Table 5.

| <Composition> | |
|---|---|
| amphoteric porous spherical particulate (Ex. 9) | 40.0% |
| carboxyvinyl polymer | 1.0% |
| propylene glycol | 10.0% |
| triethanolamine | 1.0% |
| ethanol | 30.0% |
| water | 18.0% |
| in total | 100.0% |

TABLE 5

| | | Evaluation | | |
|---|---|---|---|---|
| | | before appln. (ca 9:00) | just after appln. | before going home (ca 16:00) |
| Invention product | non-appln. part (control) | 5 | 5 | 5 |
| | appln. part | 5 | 2 | 3 |
| Comp. product (zinc oxide) | non-appln. part (control) | 5 | 5 | 5 |
| | appln. part | 5 | 4 | 4 |

Formulation Example 5 deodorant cream

The deodorant cream of the following composition was prepared and applied to the axillae to evaluate the deodorant effect thereof. The results are shown in Table 6.

| <Composition> | |
|---|---|
| amphoteric porous spherical particulate (Ex. 9) | 10.0% |
| amphoteric porous spherical particulate | 5.0% |

-continued

| <Composition> | |
|---|---|
| (Ex. 2) | |
| lactic acid | 1.0% |
| sodium lactate | 1.5% |
| cetanol | 8.0% |
| stearyl alcohol | 7.0% |
| vaseline | 6.0% |
| liquid paraffin | 5.0% |
| polyoxyethylene (20 mol adduct) sorbitan stearate | 3.0% |
| water | 53.5% |
| in total | 100.0% |

TABLE 6

| | | Evaluation | | |
|---|---|---|---|---|
| | | before appln. (ca 9:00) | just after appln. | before going home (ca 16:00) |
| Invention product | non-appln. part (control) | 5 | 5 | 5 |
| | appln. part | 5 | 1 | 2 |
| Comp. product (zinc oxide) | non-appln. part (control) | 5 | 5 | 5 |
| | appln. part | 5 | 4 | 4 |

Formulation Example 6 deodorant powder spray (powder spray type)

The deodorant powder spray of the following composition was prepared and applied to the feet to evaluate the deodorant effect thereof. The results are shown in Table 7.

| <Composition> | |
|---|---|
| Stock solution | |
| amphoteric porous spherical particulate (Ex. 9) | 20.0% |
| amphoteric porous spherical particulate (Ex. 2) | 10.0% |
| talc | 20.0% |
| aluminum hydroxychloride | 2.0% |
| isopropyl myristate | 3.0% |
| cetanol | 15.0% |
| dimethylpolysiloxane | 30.0% |
| in total | 100.0% |
| Filling | |
| above stock solution | 8.0% |
| LPG gas | 92.0% |
| in total | 100.0% |

TABLE 7

| | | Evaluation | | |
|---|---|---|---|---|
| | | before appln. (ca 9:00) | just after appln. | before going home (ca 16:00) |
| Invention product | non-appln. part (control) | 5 | 5 | 5 |
| | appln. part | 5 | 1 | 2 |
| Comp. product | non-appln. part | 5 | 5 | 5 |

TABLE 7-continued

| | | Evaluation | | |
|---|---|---|---|---|
| | | before appln. (ca 9:00) | just after appln. | before going home (ca 16:00) |
| (zinc oxide) | (control) | | | |
| | appln. part | 5 | 4 | 4 |

Below, the present invention will be described in greater detail with reference to the following Synthetic and Formulation Examples for blending for chitosan particulate, which should not be construed as limiting the scope of the invention. In the following Synthetic, Formulation and Comparative Examples, percentage is given on the weight basis unless otherwise specified.

In the Examples, the available amino group content was calculated by the following method. Further, in the Examples, the deodorant effect test with respect to the axillary and foot smells was conducted by the method described below.

<Method of calculating available amino group content>

Chitosan particulate was weighed in each amount specified in Table 8 into a 10-ml beaker, to which a $2 \times 10^{-4}$ mol/l cyclohexane solution of 4-phenylbutyric acid (standard solution) was added. 5 min later, filtration was conducted through a membrane filter, and the UV absorption of the filtrate was measured to thereby determine the absorbance $A_{abs2}$. The residual 4-phenylbutyric acid content was calculated from the above absorbance and the absorbance $A_{abs1}$ of the 4-phenylbutyric acid solution before contact with chitosan particulate according to the following formula:

residual 4-phenylbutyric acid content (%)=$A_{abs2}/A_{abs1} \times 100$ $A_{abs1}$: absorbance of 4-phenylbutyric acid solution before contact with chitosan particulate, and $A_{abs2}$: absorbance of 4-phenylbutyric acid solution after contact with chitosan particulate.

TABLE 8

| Amt. of particulate (g) | Amt. of standard soln.*[1] | Amt. of added phenylbutyric acid*[2] |
|---|---|---|
| 0.005 | 10 | $4 \times 10^{-4}$ |
| 0.01 | 5 | $1 \times 10^{-4}$ |
| 0.01 | 10 | $2 \times 10^{-4}$ |
| 0.1 | 5 | $1 \times 10^{-5}$ |
| 0.1 | 10 | $2 \times 10^{-5}$ |

Note)
*[1]: cyclohexane solution of 4-phenylbutyric acid ($2 \times 10^{-4}$ mol/l), and
*[2]: amount of 4-phenylbutyric acid per gram of chitosan.

The obtained residual 4-phenylbutyric acid content (Y) is logarithmically plotted against the amount of 4-phenylbutyric acid added per gram of chitosan particulate (X) to give at least three points, and the constants $M_0$ and $M_1$ were determined by the use of the method of least squares according to the following formula:

$$Y = M_0 + M_1 \times \log(X)$$

The value of the point of intersection (X intercept) of this graph and the function Y=0 was defined as the concentration at which the whole of the acid in the solution can be captured by the particulate (point at which the residual acid content is 0%), which was defined as the available amino group content of the particulate.

<Deodorant effect testing method>

Healthy males (aged 20 to 40) having strong axillary and foot smells were chosen and evaluated by organoleptic evaluations by four expert panelists. Specifically, first, the males having just arrived at office (around 9:00) had four expert panelists' organoleptic evaluations. Immediately after the evaluations, the deodorants prepared according to the following formulation examples were applied in appropriate amounts to the axillae and feet. Each male had the deodorant application at only one of the axillae and of the feet. The smells were evaluated just after the deodorant application. None was applied to the other axilla and foot of each male to provide controls. The evaluations involved four expert panelists, grading into any of the following six grades, the average of which was determined with respect to the axillary smell in Examples 10 to 18 while with respect to the foot smell in Examples 19 and 20. Moreover, the results of evaluation of the formulation containing zinc oxide in place of the chitosan particulate are shown as the Comparative Example.

Criterion
- 0: not smells,
- 1: slightly smells,
- 2: smells though weakly,
- 3: definitely smells,
- 4: strongly smells, and
- 5: very strongly smells.

<Synthetic examples for chitosan Particulate for use>

Synthetic Example 1

78 g of commercially available chitosan (SK-10 produced by Koyo Chemical Co., Ltd., degree of de-acetylation: 85–88%, weight-average molecular weight: 130,000) was dispersed in water. Then, 50 g of tartaric acid was added and dissolved while stirring at 60° C. Thus, a 7.8% aqueous solution of chitosan and tartaric acid was prepared.

This acidic aqueous chitosan solution was mixed with a 2.0% toluene solution of sorbitan monolaurate in a ratio of 1:1 (volumetric ratio) and agitated at a great rate of 10,000 rpm by means of a homogenizer, thereby obtaining a W/O emulsion.

Subsequently, 20 ml of the obtained emulsion was dropped into 100 ml of a 1/10N butylamine/ethanol solution under agitation to thereby effect coagulation. The coagulum was separated by filtration through a stainless steel gauze, washed with ethanol several times, recovered, and dried in a vacuum. Thus, a chitosan particulate was obtained. The obtained chitosan particulate was composed of perfectly spherical particles and had an average particle size of 10 μm.

A graph is shown in FIG. 1 in which the residual 4-phenylbutyric acid content (Y) was logarithmically plotted against the amount of 4-phenylbutyric acid added per gram of chitosan particulate (X) for calculating the available amino group content of the obtained chitosan particulate. The available amino group content of the obtained chitosan particulate and other properties are shown in Table 9.

Synthetic Example 2

80 g of commercially available chitosan (SK-10 used in Synthetic Example 1) was dispersed in water. Then, 50 g of tartaric acid was added and dissolved while stirring at 60° C. Thus, an 8.0% aqueous solution of chitosan and tartaric acid was obtained.

This acidic aqueous chitosan solution was mixed with a 5.0% cyclohexane solution of sorbitan monolaurate in a ratio of 1:1 (volumetric ratio) and agitated at a great rate of 15,000 rpm by means of a homogenizer, thereby obtaining a W/O emulsion.

Subsequently, 20 ml of the resultant emulsion was dropped into a solution of a mixture of 50 ml of amino-modified silicone (both-terminal-modified amino-modified silicone X-22-161B produced by Shin-Etsu Silicone Co., Ltd.) and 50 ml of butanol under agitation at room temperature to thereby effect coagulation. The coagulum was separated by filtration through a stainless steel gauze, washed with ethanol several times, recovered, and dried in a vacuum. Thus, a chitosan particulate was obtained. The obtained chitosan particulate was composed of particles each being nonspherical but having a definite form featured by unevenness along at least three directions and had an average particle size of 20 μm.

The available amino group content of the obtained chitosan particulate and other properties are shown in Table 9.

Synthetic Example 3

78 g of commercially available chitosan (SK-10 used in Synthetic Example 1) was dispersed in water. Then, 50 g of tartaric acid was added and dissolved while stirring at 60° C. Thus, a 7.8% aqueous solution of chitosan and tartaric acid was obtained. Separately, 0.2 g of alumina (5% relative to chitosan) was dispersed in 5 ml of water. This alumina dispersion was dispersed in 50 ml of the acidic aqueous chitosan solution.

This acidic aqueous chitosan solution having the alumina powder dispersed therein was mixed with a 2.0% cyclohexane solution of sorbitan monolaurate in a ratio of 5:5 (volumetric ratio) and agitated at a great rate of 15,000 rpm by means of a homogenizer, thereby obtaining a W/O emulsion.

Subsequently, 20 ml of the obtained emulsion was dropped into 50 ml of IN butylamine/ethanol and 50 ml of butanol under agitation at room temperature to thereby effect coagulation. The coagulum was separated by filtration through a stainless steel gauze, washed with ethanol several times, recovered, and dried in a vacuum. Thus, a chitosan particulate was obtained. The obtained chitosan particulate was composed of perfectly spherical particles and had an average particle size of 20 μm.

The available amino group content of the obtained chitosan particulate and other properties are specified in Table 9.

Synthetic Example 4

10 g of the chitosan particulate obtained in Synthetic, Example 1 was dispersed in 50 ml of ethanol, and 10 g of diethylene glycol diglycidyl ether (Denacol EX-810 produced by Nagase Industries Co.) was added and agitated at 60° C. overnight to thereby crosslink the surface of the particulate. This particulate was separated by filtration through a stainless steel gauze, washed with ethanol several times, recovered, and dried in a vacuum. Thus, a crosslinked chitosan particulate was obtained. The obtained chitosan particulate was composed of perfectly spherical particles and had an average particle size of 10 μm.

The available amino group content of the obtained chitosan particulate and other properties are shown in Table 9.

Synthetic Example 5

10 g of the chitosan particulate obtained in Synthetic Example 1 was put in 200 ml of methanol, and 200 ml of pyridine and 63 g of acetic anhydride were added under agitation and agitated at room temperature overnight. The particulate was separated by filtration through a stainless steel gauze, washed with ethanol several times, recovered, and dried in a vacuum. Thus, a partially acetylated chitosan particulate was obtained. The obtained chitosan particulate was composed of perfectly spherical particles and had an average particle size of 10 μm.

The available amino group content of the obtained chitosan particulate and other properties are shown in Table 9.

TABLE 9

| Synth. Ex. No. | Chitosan as raw material | | | Form of particulate | | | Ability to capture acid |
|---|---|---|---|---|---|---|---|
| | Synth. method | deg. of de-acetyln. (%) | wt.-av. mol. wt. | Form | av. particle size (μm) | sp. surface area (m$^2$/g) | avail. amino group cont. (mol/g) |
| 1 | emulsification, coagulation | 85–88 | 130,000 | perfectly spherical | 10 | 63.0 | $2 \times 10^{-5}$ |
| 2 | emulsification, coagulation | 85–88 | 130,000 | nonspherical definite form | 20 | 50.0 | $2 \times 10^{-5}$ |
| 3 | emulsification, coagulation | 85–88 | 130,000 | perfectly spherical | 20 | 64.0 | $1 \times 10^{-5}$ |
| 4 | emulsification, coagulation | 85–88 | 130,000 | perfectly spherical | 10 | 50.0 | $2 \times 10^{-5}$ |
| 5 | emulsification, coagulation | 85–88 | 130,000 | perfectly spherical | 10 | 50.0 | $1 \times 10^{-6}$ |

Example 10 deodorant lotion (ethanol base)

The deodorant lotion of the following composition was produced, and the deodorant effect thereof was tested with respect to the axillary smell. The results are shown in Table 10.

| <Composition of deodorant lotion> | |
|---|---|
| chitosan particulate (Synth. Ex. 1, av. particle size: 10 μm) | 10.0% |
| glycerol | 5.0% |
| water | 10.0% |
| ethanol | 75.0% |
| in total | 100.0% |

TABLE 10

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 1, av. particle size: 10 μm) | 5 | 2 |
| Comp. product | not appld. (control) | 5 | 5 |
| | zinc oxide | 5 | 3 |

Example 11 deodorant lotion (volatile silicone base)

The deodorant lotion of the following composition was produced, and the deodorant effect thereof was tested with respect to the axillary smell. The results are shown in Table 11.

| <Composition of deodorant lotion> | |
|---|---|
| chitosan particulate (Synth. Ex. 2, av. particle size: 20 μm) | 50.0% |
| dimethylsilicone | 10.0% |
| methylpolysiloxane | 40.0% |
| in total | 100.0% |

TABLE 11

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 2, av. particle size: 20 μm) | 5 | 1 |
| Comp. product | not appld. (control) | 5 | 5 |
| | zinc oxide | 5 | 3 |

Example 12 deodorant stick

The deodorant stick of the following composition was produced, and the deodorant effect thereof was tested with respect to the axillary smell. The results are shown in Table 12.

| <Composition of deodorant stick> | |
|---|---|
| chitosan particulate (Synth. Ex. 1, av. particle size: 10 μm) | 20.0% |
| stearyl alcohol | 60.0% |
| talc | 20.00% |
| in total | 100.0% |

TABLE 12

| Compsn. | | Evaluation | |
|---|---|---|---|
| | | before appln. (ca 9:00) | just after appln. |
| Invention product | not appld. (control) | 5 | 5 |
| | chitosan particulate (Synth. Ex. 1, av. particle size: 10 μm) | 5 | 1 |
| Comp. product | not appld. (control) | 5 | 5 |
| | zinc oxide | 5 | 3 |

Example 13 liquid-spray deodorant

The liquid-spray deodorant of the following composition was produced, and the deodorant effect thereof was tested with respect to the axillary smell. The results are shown in Table 13.

| <Composition of liquid-spray deodorant> | |
|---|---|
| Stock solution | |
| chitosan particulate (Synth. Ex. 4, av. particle size: 10 μm) | 12.5% |
| isopropyl myristate | 5.0% |
| glycerol | 5.0% |
| water | 5.0% |
| ethanol | 72.5% |
| in total | 100.0% |
| Filling | |
| above stock solution | 35.0% |
| LPG gas | 65.0% |
| in total | 100.0% |

TABLE 13

| Compsn. | | Evaluation | |
|---|---|---|---|
| | | before appln. (ca 9:00) | just after appln. |
| Invention product | not appld. (control) | 5 | 5 |
| | chitosan particulate (Synth. Ex. 4, av. particle size: 10 μm) | 5 | 2 |
| Comp. product | not appld. (control) | 5 | 5 |
| | zinc oxide | 5 | 3 |

Example 14 powder-spray deodorant

The powder-spray deodorant of the following composition was produced, and the deodorant effect thereof was tested with respect to the axillary smell. The results are shown in Table 14.

| <Composition of powder-spray deodorant> | |
|---|---|
| Stock solution | |
| chitosan particulate (Synth. Ex. 1, av. particle size: 10 μm) | 5.0% |
| talc | 46.5% |
| myristic ester | 25.0% |
| dimethylsilicone | 5.0% |
| methylpolycyclosiloxane | 18.5% |
| in total | 100.0% |
| Filling | |
| above stock solution | 8.0% |
| LPG gas | 92.0% |
| in total | 100.0% |

TABLE 14

| Compsn. | | Evaluation | |
|---|---|---|---|
| | | before appln. (ca 9:00) | just after appln. |
| Invention product | not appld. (control) | 5 | 5 |
| | chitosan particulate (Synth. Ex. 1, av. particle size: 10 μm) | 5 | 1 |
| Comp. product | not appld. (control) | 5 | 5 |
| | zinc oxide | 5 | 3 |

Example 15 gel deodorant

The gel deodorant of the following composition was produced, and the deodorant effect thereof was tested with respect to the axillary smell. The results are shown in Table 15.

| <Composition of gel deodorant> | |
|---|---|
| chitosan particulate (Synth. Ex. 5, av. particle size: 10 μm) | 40.0% |
| carboxyvinyl polymer | 1.0% |
| propylene glycol | 10.0% |
| triethanolamine | 1.0% |
| ethanol | 30.0% |
| water | 18.0% |
| in total | 100.0% |

TABLE 15

| Compsn. | | Evaluation | |
|---|---|---|---|
| | | before appln. (ca 9:00) | just after appln. |
| Invention product | not appld. (control) | 5 | 5 |
| | chitosan particulate (Synth. Ex. 5, av. particle size: 10 μm) | 5 | 2 |
| Comp. product | not appld. (control) | 5 | 5 |
| | zinc oxide | 5 | 3 |

Example 16 creamy (O/W-cream) deodorant

The O/W-cream deodorant of the following composition was produced, and the deodorant effect thereof was tested with respect to the axillary smell. The results are shown in Table 16.

| <Composition of creamy deodorant> | |
|---|---|
| chitosan particulate (Synth. Ex. 3, av. particle size: 20 μm) | 10.0% |
| cetanol | 9.0% |
| stearyl alcohol | 8.0% |
| vaseline | 7.0% |
| liquid paraffin | 7.0% |
| polyoxyethylene (20 mol adduct) sorbitan stearate | 3.0% |
| water | 56.0% |
| in total | 100.0% |

TABLE 16

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 3, av. particle size: 20 μm) | 5 | 2 |
| Comp. product | not appld. (control) | 5 | 5 |
| | zinc oxide | 5 | 3 |

Example 17 creamy (O/W-cream) deodorant

The O/W-cream deodorant of the following composition was produced, and the deodorant effect thereof was tested with respect to the axillary smell. The results are shown in Table 17.

| <Composition of creamy deodorant> | |
|---|---|
| chitosan particulate (Synth. Ex. 4, av. particle size: 10 μm) | 10.0% |
| beeswax | 10.0% |
| cetyl alcohol | 5.0% |
| glyceryl monostearate | 2.0% |
| polyoxyethylene (20 mol adduct) sorbitan stearate | 2.0% |
| water | 61.0% |
| squalane | 10.0% |
| in total | 100.0% |

TABLE 17

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 4, av. particle size: 10 μm) | 5 | 2 |
| Comp. product | not appld. (control) | 5 | 5 |
| | zinc oxide | 5 | 3 |

Example 18 creamy (W/O-cream) deodorant

The W/O-cream deodorant of the following composition was produced, and the deodorant effect thereof was tested with respect to the axillary smell. The results are shown in Table 18.

| <Composition of creamy deodorant> | |
|---|---|
| chitosan particulate (Synth. Ex. 5, av. particle size: 10 μm) | 40.0% |
| solid paraffin | 8.0% |
| beeswax | 8.0% |
| vaseline | 12.0% |
| polyoxyethylene (20 mol adduct) sorbitan stearate | 4.0% |
| liquid paraffin | 10.0% |
| water | 18.0% |
| in total | 100.0% |

TABLE 18

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 5, av. particle size: 10 μm) | 5 | 2 |
| Comp. product | not appld. (control) | 5 | 5 |
| | zinc oxide | 5 | 3 |

Example 19 liquid-spray deodorant

The liquid-spray deodorant of the following composition was produced, and the deodorant effect thereof was tested with respect to the foot smell. The results are shown in Table 19.

| <Composition of liquid-spray deodorant> | |
|---|---|
| Stock solution | |
| chitosan particulate (Synth. Ex. 1, av. particle size: 10 μm) | 12.5% |
| isopropyl myristate | 5.0% |
| glycerol | 5.0% |
| water | 5.0% |
| ethanol | 72.5% |
| in total | 100.0% |
| Filling | |
| above stock solution | 35.0% |
| LPG gas | 65.0% |
| in total | 100.0% |

TABLE 19

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 1, av. particle size: 10 μm) | 5 | 1 |
| Comp. product | not appld. (control) | 5 | 5 |
| | zinc oxide | 5 | 3 |

Example 20 powder-spray deodorant

The powder-spray deodorant of the following composition was produced, and the deodorant effect thereof was tested with respect to the foot smell. The results are shown in Table 20.

<Composition of powder-spray deodorant>

Stock solution

| | |
|---|---|
| chitosan particulate (Synth. Ex. 2, av. particle size: 20 µm) | 5.0% |
| talc | 46.5% |
| myristic ester | 25.0% |
| dimethylsilicone | 5.0% |
| methylpolycyclosiloxane | 18.5% |
| in total | 100.0% |

Filling

| | |
|---|---|
| above stock solution | 8.0% |
| LPG gas | 92.0% |
| in total | 100.0% |

TABLE 20

| | | Evaluation | |
|---|---|---|---|
| | Compsn. | before appln. (ca 9:00) | just after appln. |
| Invention product | not appld. (control) | 5 | 5 |
| | chitosan particulate (Synth. Ex. 2, av. particle size: 20 µm) | 5 | 1 |
| Comp. product | not appld. (control) | 5 | 5 |
| | zinc oxide | 5 | 3 |

Example 21

Each of about 20 axillary smell test subjects had a cotton pat fitted in the axilla for one day, and the cotton pats were collected and immersed in methanol to thereby recover the smell (about 2 l). The methanol was concentrated to about 60 ml and used as an axillary smell sample.

A filter paper of 70 mm in diameter was placed on the bottom of a 300-ml beaker and impregnated with 0.35 g of the above axillary smell sample. It was allowed to stand still at room temperature for 3 min, and 0.2 g of the deodorant of the following composition was spread thereover. It was allowed to stand still at room temperature for 2 min, and the same four expert panelists' six-level-grading evaluation as in Examples 10 to 20 was carried out with one having no deodorant applied thereto as a control. The same evaluation was carried out with the use of zinc oxide as the comparative item. The results are shown in Table 21.

<Composition of deodorant>

| | |
|---|---|
| chitosan particulate | 2.0% |
| ethanol | 20.0% |
| Silicone SH245 (produced by Toray Dow Silicone (K.K)) | balance |

TABLE 21

| | Comp. product. | | Invention product chitosan particulate | |
|---|---|---|---|---|
| Compsn. | not appld. | zinc oxide | odd-shaped (Synth. Ex. 2) | spherical (Synth. Ex. 1) |
| Evaluation | 5 | 3 | 1 | 1 ~ 2 |

Now the present invention will be described in greater detail with reference to the following Examples relating to polysiloxanes, which should not be construed as limiting the scope of the invention.

Synthetic Example 6 (exemplary synthesis of polysiloxane modified with long-chain alkyl groups at both its terminals)

400 ml of dry cyclohexane, 3 ml of tetramethylethylenediamine and 12.5 ml (0.02 mol) of n-butyl-lithium (1.6 mol/l) were fed into a 1-l autoclave purged with nitrogen. 8.2 l of ethylene gas was introduced into the reaction system while holding the temperature of the reaction system and the ethylene gas pressure at 30° C. and 2 kg/cm², respectively. Thereafter, the ethylene gas was expelled and replaced by nitrogen. The resultant polymerization mixture was dropped under a nitrogen stream into a solution of 11.8 g of octamethylcyclotetrasiloxane in 10 ml of dry cyclohexane separately provided in a 1-l short-necked round-bottomed flask in advance. After the completion of the dropping, a reaction was conducted at 30° C. for 1 hour, The reaction mixture was poured into 2 l of methanol, agitated for 1 hours and filtered in a vacuum to thereby collect the formed solids. The solids were dried in a vacuum oven at 50° C. for 24 hr. Thus, a white waxy solid was obtained. The product yield was 12.0 g. GPC analysis (using the apparatus manufactured by Waters Associate Inc., o-dichlorobenzene, 135° C., calibrated with standard sample of polyethylene) showed that the number-average molecular weight and the molecular weight distribution of the product were 610 and 1.03, respectively.

In the $^1$H-NMR analysis (using the apparatus manufactured by Bruker, 200 MHz, chloroform-d, 50° C., TMS used as standard), the signals assignable to the methyl group bonded to the silyl group, the methylene group bonded to the silyl group, the initiation terminal methyl group and the methylene group of the principal chain were observed at –0.05 ppm (singlet), 0.4 ppm (triplet), 0.8 ppm (triplet) and about 1.2 ppm, respectively. The terminal silanol group introduction ratio was found to be 99% from the individual signal integral ratios. The number of introduced siloxane units was 1.4 per ethylene terminal.

Subsequently, 12.0 g of the synthesized silanolterminated polyethylene, 88 g of octamethylcyclotetrasiloxane and 100 ml of toluene were put in a 1-l separable flask equipped with a condenser and heated on an oil bath until reflux of the toluene started. When all the starting compounds were homogeneously dissolved, 0.01 g of potassium hydroxide was added. The reflux was continued for 48 hours as it was. Thereafter, 0.18 ml of a 1N alcoholic hydrochloric acid solution was added and satisfactorily agitated. Water was added, and the inorganic salt formed thereby was extracted after confirming that the pH value of the solution was 7. Water washing was conducted thrice under heating and the condenser was replaced by a Dean-Stark tube reflux condenser to effect toluene reflux until the dehydration was completed. The toluene was distilled off, thereby obtaining a rubbery white wax. The product yield was 96 g.

GPC analysis (using the apparatus manufactured by Waters Associate Inc., o-dichlorobenzene, 135° C., in terms of polystyrene) showed that the weight-average molecular weight and the molecular weight distribution of the product were 18,600 and 2.03, respectively.

In the $^1$H-NMR analysis (using the apparatus manufactured by Bruker, 200 MHz, chloroform-d, 50° C., TMS used as standard), the signals assignable to the methyl group bonded to the silyl group, the methylene group bonded to the Silyl group, the initiation terminal methyl group and the methylene group of the polyethylene chain were observed at −0.05 ppm (singlet), 0.4 ppm (triplet), 0.8 ppm (triplet) and about 1.2 ppm, respectively. The weight ratio of the polyethylene moiety to the siloxane moiety was found to be 10:90 from the individual signal integration ratios.

A temperature-programmed DSC measurement showed that the melting point of the product (apex of endothermic peak) was 92° C.

Synthetic Example 7 (exemplary synthesis of side-chain-alkyl-modified polysiloxane)

79 g of methylhydrogenpolysiloxane (PS120 produced by Chisso Corporation, molecular weight: 2270), 20 g of Dialene 18 (1-octadecene produced by Mitsubishi Chemical Industries, Ltd.) and 100 ml of toluene were fed into a 1 l separable flask equipped with a condenser. Chloroplatinic acid was added in an amount of 100 ppm in terms of platinum and reacted at 80° C. for 24 hours. The reaction product was purified by reprecipitation twice with the use of ethanol, thereby obtaining a brownish soft wax. The yield and melting point of the wax were 99 g and 23° C., respectively. The $^1$H-NMR and IR analyses showed that the contents of residual terminal hydrogen and olefin were 0% and 1%, respectively.

Synthetic Example 8 (exemplary synthesis of both-terminalalkyl-modified polysiloxane)

38 g of terminal-hydrogen-modified polysiloxane (PS537 produced by Chisso Corporation, molecular weight: 440), 74 g of Dialene 208 (mixture of $C_{20-28}$ or higher α-olefins produced by Mitsubishi Chemical Industries, Ltd.) and 100 ml of toluene were into a 1-l separable flask equipped with a condenser. Chloroplatinic acid was added in an amount of 100 ppm in terms of platinum and reacted at 80° C. for 24 hours. The reaction product was purified by reprecipitation, thereby obtaining a brownish soft wax. The yield and melting point of the wax were 98 g and 42° C., respectively. The $^1$H-MMR and IR analyses showed that the contents of residual terminal hydrogen and olefin were 1% and 8%, respectively.

Test Example 1

Compositions of Table 22 each in the form of a suspension were prepared with the use of the polysiloxanes obtained in the above Synthetic Examples 6 to 8 and also with the use of paraffin wax (melting point: 68° C., produced by Nippon Seiro Co., Ltd.) for comparison as wax components. Each of these suspension compositions was applied to a leather, and the surface thereof was rubbed with a leather at 37° C. The residual coating content was measured and the surface condition was observed. Further, each of the compositions was applied to a Cellophane film, and the moisture permeability (unit: g/m$^2$-24 hr/10 μm, calcium chloride used as moisture absorbent, measured at 25° C. in 65% RH) was determined. The results are shown in Table 22.

TABLE 22

|  |  | Invention product | | | Comp. product |
|---|---|---|---|---|---|
|  |  | 1 | 2 | 3 | 4 |
| Compsn. (wt. %) | polysiloxane modified with long-chain alkyls at both terminals (Synth. Ex. 1) | 10 | — | — | — |
|  | side-chain-alkyl-modified polysiloxane (Synth. Ex. 2) | — | 10 | — | — |
|  | both-terminal-alkyl-modified polysiloxane (Synth. Ex. 3) | — | — | 10 | — |
|  | paraffin wax (m.p.: 68° C., prepd. by Nippon Seiro Co., Ltd.) | — | — | — | 10 |
|  | octamethyltetracyclosiloxane (Toshiba Silicone TSF404) | 30 | 30 | 30 | 30 |
|  | isopentane | 50 | 50 | 50 | 50 |
|  | ethanol | 10 | 10 | 10 | 10 |
| Test item | residual coating content (wt. %) | 78 | 13 | 23 | 79 |
|  | observation of surface | waxy | oily | oily | waxy |
|  | moisture permeability (g/m$^2$-24hr/10 μm) | 790 | 14 | 121 | 2 |

Synthetic Example 9 (exemplary synthesis of amphoteric porous particulate)

Water was added to 80 g of commercially available chitosan (SK-10 produced by Koyo Chemical Co., Ltd., degree of de-acetylation: 85–88%, weight-average molecular weight: 130,000) until the total weight amounted to 900 g. 34.6 g of methacrylic acid (equimolar to the monosaccharide units of the chitosan) was added and dissolved while stirring at 60° C., thereby preparing an aqueous solution of chitosan and methacrylic acid. A solution obtained by dissolving 3 g of potassium persulfate in 100 g of ion-exchanged water was added to the above aqueous solution and agitated at room temperature for a few minutes.

The chitosan solution was mixed with a 1.0% by weight cyclohexane solution of sorbitan monolaurate in a ratio of 5:5 (volumetric ratio) and agitated at a great rate of 15,000 rpm by means of a homogenizer, thereby obtaining a W/O emulsion.

A polymerization reaction was effected at 70° C. for 2 hours, and the reaction mixture was cooled to room temperature, dropped into ethanol in a molar (volumetric) proportion of 1:5 under agitation. Agitation was continued for 30 min, and any agglomerate was removed by decantation. Immersion in ethanol and agitation followed by filtration through a Buchner funnel were conducted thrice. Then, vacuum drying was effected, thereby obtaining a particulate. The obtained particulate had an average particle size of 12 μm, was composed of perfectly spherical particles, and had a specific surface area of 50 m$^2$/g.

Example 22

A deodorant stick was prepared according to the composition of Table 23 with the use of the polysiloxane modified with long-chain alkyl groups at both its terminals which was synthesized in Synthetic Example 6 and the amphoteric porous particulate which was synthesized in Synthetic Example 9.

TABLE 23

| Ingredients | Amt. (wt. %) |
| --- | --- |
| polysiloxane modified with long-chain alkyls at both terminals (Synth. Ex. 6) | 20 |
| amphoteric porous particulate (Synth. Ex. 9) | 10 |
| dimethylsilicone | 10 |
| octamethyltetracyclosiloxane | 30 |
| isopropyl palmitate | 20 |
| stearyl alcohol | 5 |
| ceresin | 5 |
| in total | 100 |

Examples 23 and 24

Deodorant sticks were prepared in the same manner as in Example 22 with the use of the same amounts of the side-chain-alkyl-modified polysiloxane synthesized in Synthetic Example 7 and both-terminal-alkyl-modified polysiloxane synthesized in Synthetic Example 8, respectively, in place of the polysiloxane modified with long-chain alkyl groups at both its terminals which was synthesized in Synthetic Example 6.

Example 25

A deodorant stick was prepared in the same manner as in Example 22 with the use of the same amount of hybrid zinc oxide in place of the amphoteric porous particulate synthesized in Synthetic Example 9.

Comparative Example 3

A deodorant stick was prepared in the same manner as in Example 22 with the use of the same amount of paraffin wax (melting point: 68° C., produced by Nippon Seiro Co., Ltd.) in place of the polysiloxane modified with long-chain alkyl groups at both its terminals which was synthesized in Synthetic Example 6.

Test Example 2

The deodorant effect of each of the deodorant sticks prepared in Examples 22 to 25 and Comparative Example 3 was tested by the following method. The results are shown in Table 24.

<Testing method>

Healthy males (aged 20 to 40) having strong axillary or foot smells were chosen and evaluated by organoleptic evaluations by four expert panelists. Specifically, the males had four expert panelists' organoleptic evaluations at 9 o'clock in the morning. Immediately after the evaluations, the deodorant sticks prepared in the above examples were applied in appropriate amounts to the axillae and feet. Each male had the deodorant application at only one of the axillae and of the feet. The smells were evaluated just after the deodorant application, 1 hour later and 8 hours later. Moreover, for comparison, similar evaluations were made with respect to each of the amphoteric porous particulate synthesized in Synthetic Example 9 and the hybrid zinc oxide alone. The evaluation involved four expert panelists' grading into any of the following six grades. Further, the appearance of each of the surfaces having the deodorant applied thereto was observed 8 hours after the application.

Criterion

0: not smells,
1: slightly smells,
2: smells though weakly,
3: definitely smells,
4: strongly smells, and
5: very strongly smells.

TABLE 24

| | before appln. | just after appln. | 1 h later | 8 h later | appearance of surface having deodorant appld. thereto |
| --- | --- | --- | --- | --- | --- |
| Ex. 22 | 5 | 0 | 0 | 0 | smooth, appln. hardly recognized |
| Ex. 23 | 5 | 1 | 3 | 3 | trace of oily substance left |
| Ex. 24 | 5 | 0 | 1 | 2 | sticky as if oil were applied |
| Ex. 25 | 5 | 0 | 3 | 3 | smooth, white residue observed |
| Comp. Ex. 3 | 5 | 0 | 3 | 4 | whitely cracking |
| not appld. | 5 | 5 | 5 | 5 | — |
| amphoteric porous particulate (Synth. Ex. 9) | 5 | 0 | 4 | 4 | scarcely any residue |
| hybrid zinc oxide | 5 | 3 | 4 | 5 | scarcely any residue |

Example 26

A stock solution was prepared according to the composition of Table 25 with the use of the polysiloxane modified with long-chain alkyl groups at both its terminals which was synthesized in Synthetic Example 6 and the amphoteric porous particulate which was synthesized in Synthetic Example 9. 10% by weight of the above stock solution and 90% by weight of LPG gas were fed into a spray can, thereby preparing a deodorant spray.

TABLE 25

| Ingredients (stock soln.) | Amt. (wt. %) |
| --- | --- |
| polysiloxane modified with long-chain alkyls at both terminals (Synth. Ex. 6) | 25 |
| amphoteric porous particulate (Synth. Ex. 9) | 10 |
| talc | 10 |
| isopropyl myristate | 5 |
| cetanol | 15 |
| octamethyltetracyclosiloxane | 25 |
| dimethylsilicone | 10 |
| in total | 100 |

Examples 27 and 28

Deodorant sprays were prepared in the same manner as in Example 26 with the use of the same amounts of the side-chain-alkyl-modified polysiloxane synthesized in Synthetic Example 7 and the both-terminal-alkyl-modified polysiloxane synthesized in Synthetic Example 8, respectively, in place of the polysiloxane modified with long-chain alkyl groups at both its terminals which was synthesized in Synthetic Example 6.

Example 29

A deodorant spray was prepared in the same manner as in Example 26 with the use of the same amount of hybrid zinc oxide in place of the amphoteric porous particulate synthesized in Synthetic Example 9.

Comparative Example 4

A deodorant spray was prepared in the same manner as in Example 26 with the use of the same amount of paraffin wax (melting point: 68° C., produced by Nippon Seiro Co., Ltd.) in place of the polysiloxane modified with long-chain alkyl groups at both its terminals which was synthesized in Synthetic Example 6.

Test Example 3

The deodorant effect of each of the deodorant sprays prepared in Examples 26 to 29 and Comparative Example 2 was tested in the same manner as in Test Example 2. The test results are shown in Table 26.

TABLE 26

|  | before appln. | just after appln. | 1 h later | 8 h later | appearance of surface having deodorant appld. thereto |
|---|---|---|---|---|---|
| Ex. 26 | 5 | 0 | 0 | 1 | appln. hardly recognized |
| Ex. 27 | 5 | 1 | 3 | 4 | trace of oily substance left |
| Ex. 28 | 5 | 0 | 1 | 3 | trace of oily substance left |
| Ex. 29 | 5 | 0 | 3 | 3 | trace of white residue observed |
| Comp. Ex. 4 | 5 | 3 | 4 | 4 | looks as if powder were sprayed |
| not appld. | 5 | 5 | 5 | 5 | — |
| amphoteric porous aprticulate (Synth. Ex. 9) | 5 | 0 | 4 | 4 | scarcely any residue |
| hybrid zinc oxide | 5 | 3 | 4 | 5 | scarcely any residue |

We claim:

1. An amphoteric porous particulate comprising a basic polysaccharide and a polymer of an organic acid containing a reactive vinyl group or a salt thereof and having an average particle size of 50 μm or less,
   wherein said amphoteric porous particulate comprises spherical particles.

2. The porous particulate according to claim 1, which has a specific surface area of 10 to 300 m²/g.

3. The porous particulate according to claim 1, wherein the basic polysaccharide is chitosan.

4. The porous particulate according to claim 1, wherein the organic acid containing a reactive vinyl group or salt thereof is methacrylic acid or a salt thereof.

5. A process for producing a porous particulate defined in claim 1, which comprises emulsifying or suspending an aqueous solution containing a basic polysaccharide and an organic acid having a reactive vinyl group in a hydrophobic solvent and thereafter effecting polymerization thereof.

6. The process for producing a porous particulate according to claim 5, wherein, after the polymerization, a polymerization reaction mixture is dropped into or added at once to an organic solvent containing a base to thereby precipitate a porous particulate.

7. The process for producing a porous particulate according to claim 5, wherein the organic acid is used in a molar amount of 0.1 to 500 times the number of moles of monosaccharide units composing the basic polysaccharide.

8. A cosmetic composition characterized by comprising the porous particulate defined in claim 1.

9. The cosmetic composition according to claim 8, which contains the amphoteric porous particulate in an amount of 0.1 to 70% by weight.

10. The cosmetic composition according to claim 8, which is a deodorant.

11. A deodorant composition comprising the porous particulate defined in claim 1 and an oil capable of dispersing the porous particulate.

12. The amphoteric porous particulate of spherical fine particles according to claim 1, which comprises a basic polysaccharide and a polymer of an organic acid containing a reactive vinyl group and having an average particle size of 50 μm or less.

13. The porous particulate according to claim 1, wherein the basic polysaccharide is chitosan.

14. A deodorant composition comprising a chitosan particulate having an average particle size of 0.01 to 50 μm as the deodorant.

15. The deodorant composition according to claim 14, wherein the chitosan particulate has a specific surface area of 10 to 300 m²/g.

16. The deodorant composition according to claim 14, wherein the chitosan particulate has an available amino group content of $1.0 \times 10^{-7}$ to $1.0 \times 10^{-2}$ mol/g.

17. The deodorant composition according to claim 14, wherein the chitosan particulate is composed of spherical fine particles.

18. A deodorant composition characterized by comprising the porous particulate defined in claim 1 and 0.01 to 99% by weight of a polysiloxane having long-chain alkyl groups as an oil, said polysiloxane having a melting point of at least 20° C.

19. The deodorant composition according to claim 14, which further comprises 0.01 to 99% by weight of a polysiloxane having long-chain alkyl groups and a melting point of 20° C. or above.

20. A deodorant composition comprising a deodorant and 0.01 to 99% by weight of a polysiloxane having long-chain alkyl groups and a melting point of 20° C. or above.

21. The deodorant composition according to claim 20, characterized that the melting point of the polysiloxane is in the range of 60° to 140° C. and the polysiloxane has long-chain alkyl groups at both its molecular terminals.

22. The deodorant composition according to claim 20, characterized that the proportion of the long-chain alkyl group portion of the polysiloxane having long-chain alkyl groups in total is in the range of 0.5 to 40% by weight.

23. The deodorant composition according to claim 20, characterized by comprising a basic substance.

24. The deodorant composition according to claim 20, characterized by containing an amphoteric porous particulate comprising a basic polysaccharide and a polymer of an organic acid containing a reactive vinyl group or a salt thereof and having an average particle size of 50 μm or less.

25. The deodorant composition according to claim 20, wherein the polysiloxane is represented by the general formula (I):
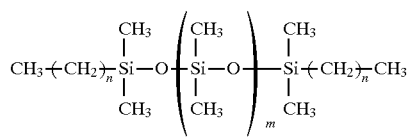
(wherein n is the average number of carbon atoms of long-chain alkyl groups, satisfying the relationship (n+1) $\geq 30$, and m is a number of 0 or above).
26. The composition according to claim 25, wherein m is a number of 100 to 5000.
* * * * *